United States Patent [19]

Boden

[11] Patent Number: 4,742,044

[45] Date of Patent: May 3, 1988

[54] ARALKOXY, ALKOXY, ALKADIENYLOXY AND ALKENYLOXY-1,3,2-DIOXABORINANE DERIVATIVES AND USES THEREOF IN AUGMENTING OR ENHANCING THE AROMA OF PERFUME COMPOSITIONS, PERFUMED ARTICLES AND PERFUMED POLYMERS

[75] Inventor: Richard M. Boden, Ocean, N.J.

[73] Assignee: International Flavors & Fragrances Inc., New York, N.Y.

[21] Appl. No.: 86,812

[22] Filed: Aug. 19, 1987

[51] Int. Cl.$^4$ .............................................. A61K 7/46
[52] U.S. Cl. .......................................... 512/12; 512/7; 512/8; 512/11; 512/22; 512/23; 558/288
[58] Field of Search ...................... 558/288; 512/8, 11, 512/22, 23, 12, 7

[56] References Cited

U.S. PATENT DOCUMENTS

| | | | |
|---|---|---|---|
| 2,839,564 | 6/1958 | Garner | 558/288 |
| 3,189,637 | 6/1965 | Bengelsdoff | 558/288 |
| 3,564,091 | 2/1971 | Degray | 424/185 |
| 4,146,506 | 3/1979 | Bruns et al. | 512/12 |
| 4,391,999 | 7/1983 | Boden | 568/840 |

FOREIGN PATENT DOCUMENTS 722538  1/1955  United Kingdom ................ 558/288

OTHER PUBLICATIONS

Arctander, "Perfume and Flavor Chemicals, Aromatic Chemicals", vol. 1, Monographs 1427, 669, 670 and 2538 (1969).

Primary Examiner—Werren B. Lone
Attorney, Agent, or Firm—Arthur L. Liberman

[57] ABSTRACT

Described are the aralkoxy, alkoxy, alkadienyloxy and alkenyloxy-1,3,2-dioxaborinane derivatives defined according to the genus:

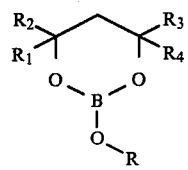

(wherein $R_1$, $R_2$, $R_3$ and $R_4$ are the same or different hydrogen, methyl and ethyl; and wherein R represents $C_6$ straight chain alkenyloxy; $C_{10}$ branched chain alkenyloxy; $C_{12}$ aralkoxy; $C_{12}$ branched chain alkoxy; or $C_{10}$ branched chain alkadienyloxy) and uses thereof in augmenting or enhancing the aroma of perfume compositions, perfumed articles, particularly drier-added fabric softener articles and perfumed polymers.

17 Claims, 21 Drawing Sheets

GLC PROFILE FOR EXAMPLE II.
REACTION MIXTURE

GLC PROFILE FOR EXAMPLE II.
CRUDE

FIG. 3 GLC PROFILE FOR BULKED FRACTIONS 3 & 4 OF EXAMPLE II.

FIG. 4 NMR SPECTRUM FOR EXAMPLE II.

IR SPECTRUM FOR EXAMPLE II.

GLC PROFILE FOR EXAMPLE III. REACTION MIXTURE

GLC PROFILE FOR EXAMPLE III. CRUDE

NMR SPECTRUM FOR EXAMPLE III.

IR SPECTRUM FOR EXAMPLE III.

GLC PROFILE FOR EXAMPLE IV.
CRUDE

FIG.11 NMR SPECTRUM FOR EXAMPLE IV.

GLC PROFILE FOR EXAMPLE V.
CRUDE

FIG.15 NMR SPECTRUM FOR EXAMPLE V.

IR SPECTRUM FOR EXAMPLE V

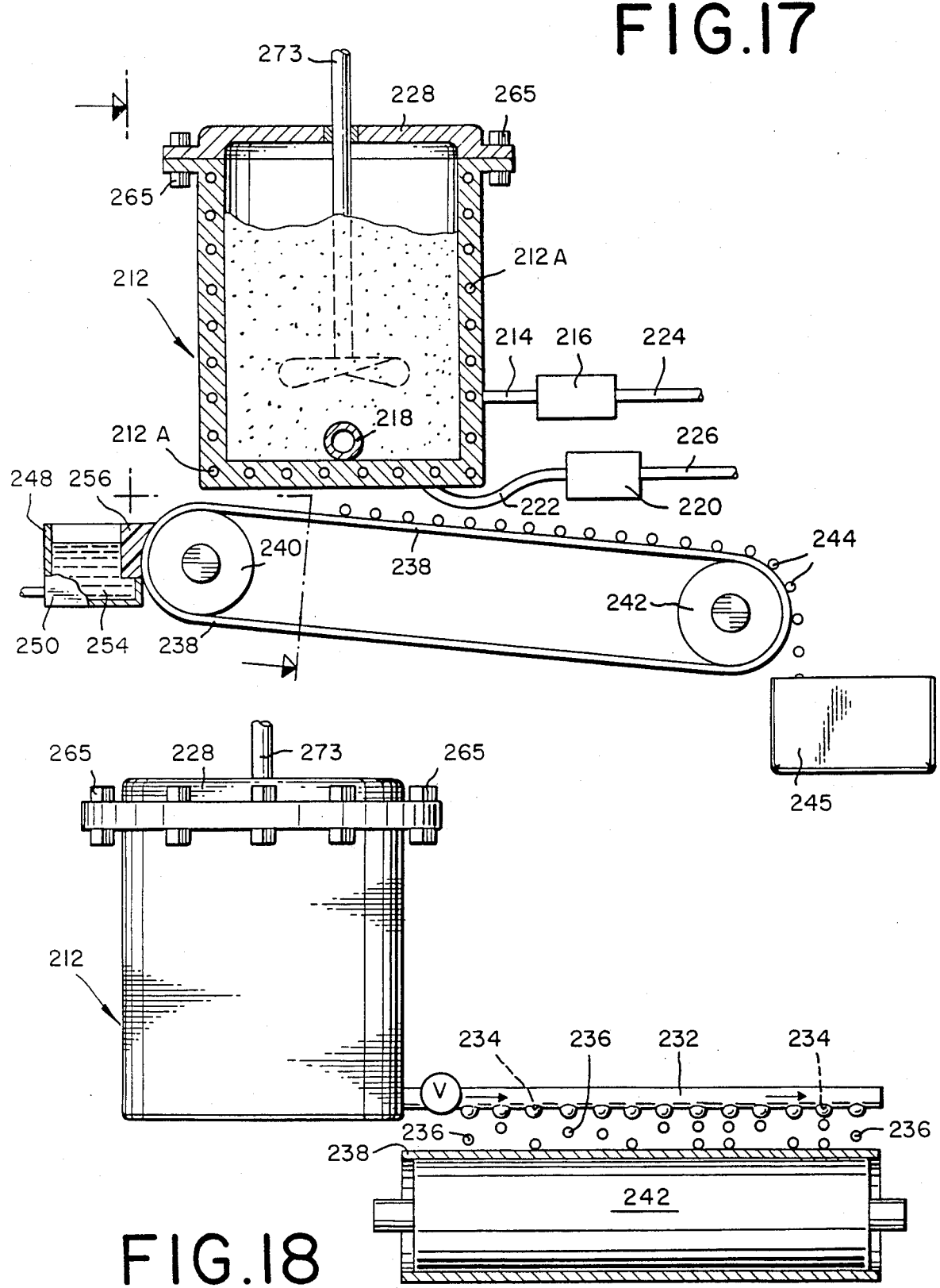

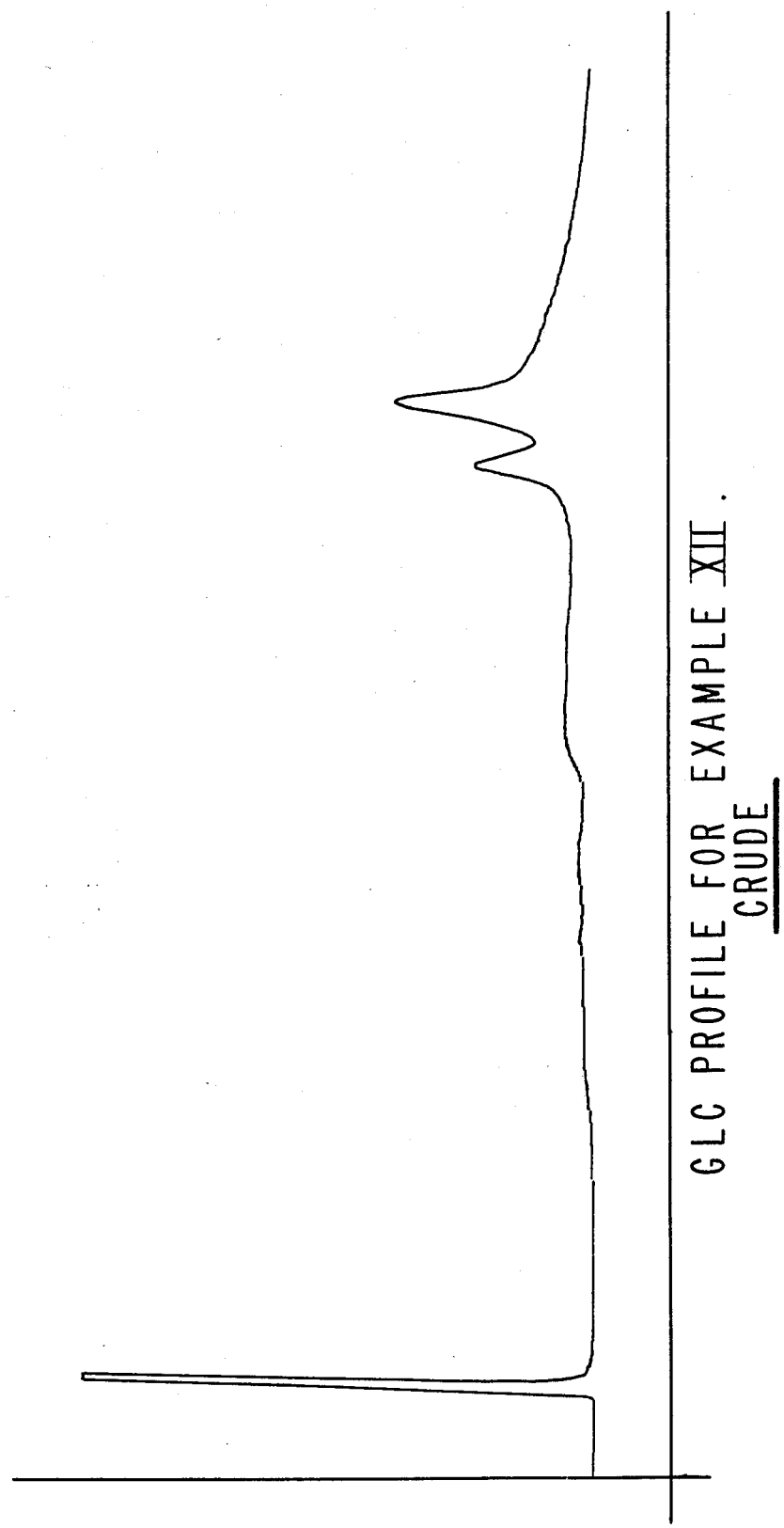

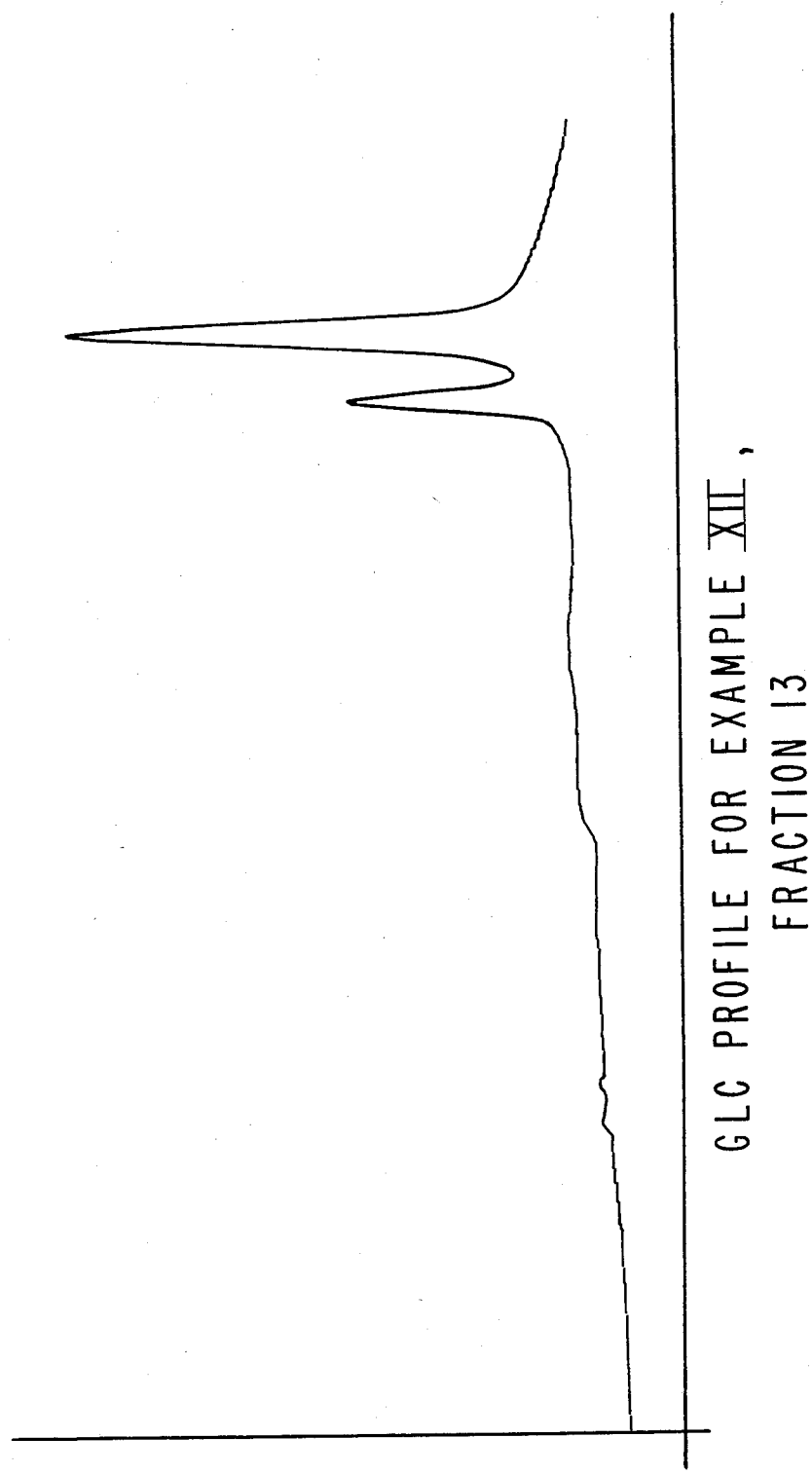

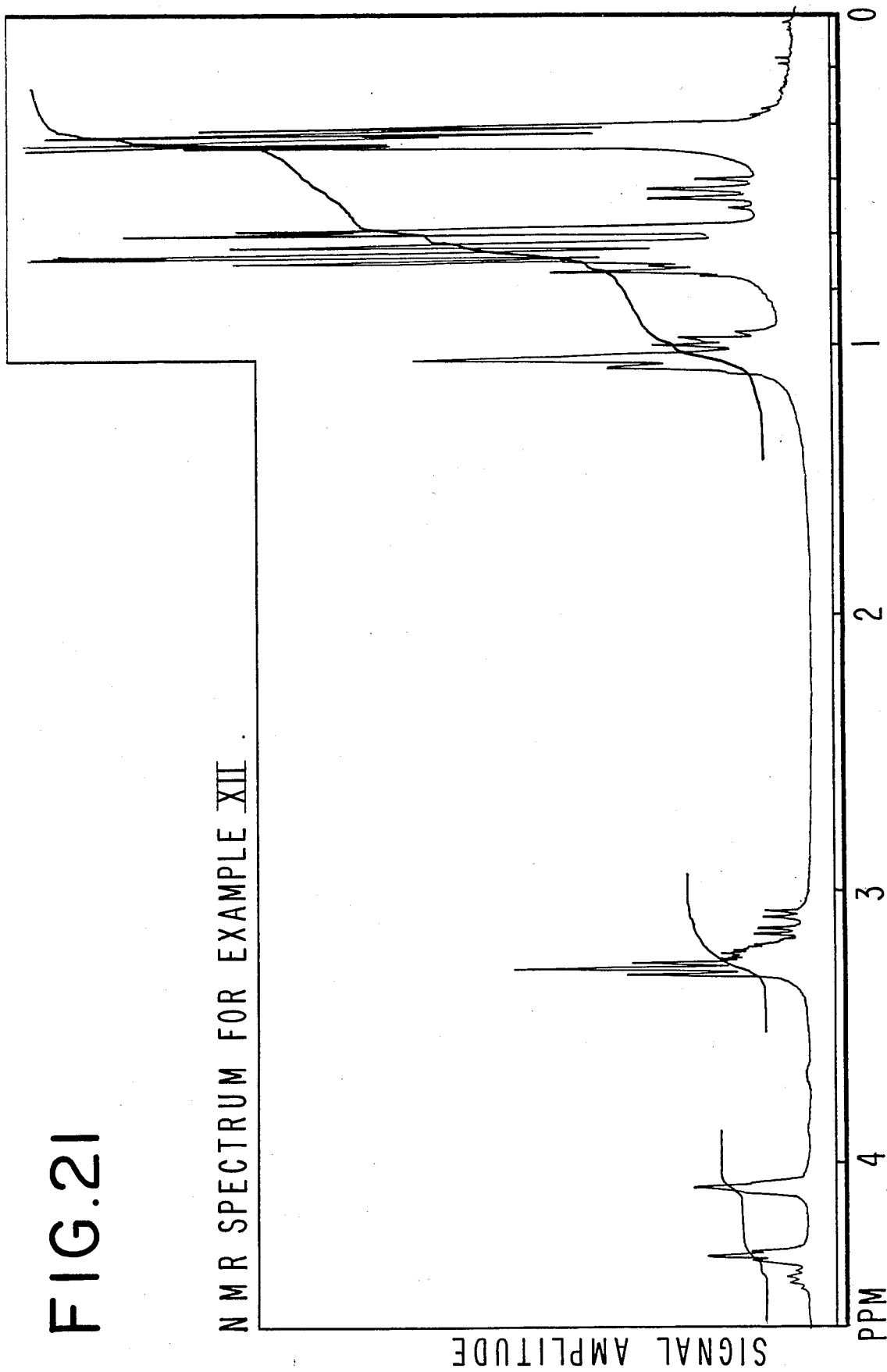
FIG. 21 NMR SPECTRUM FOR EXAMPLE XII.

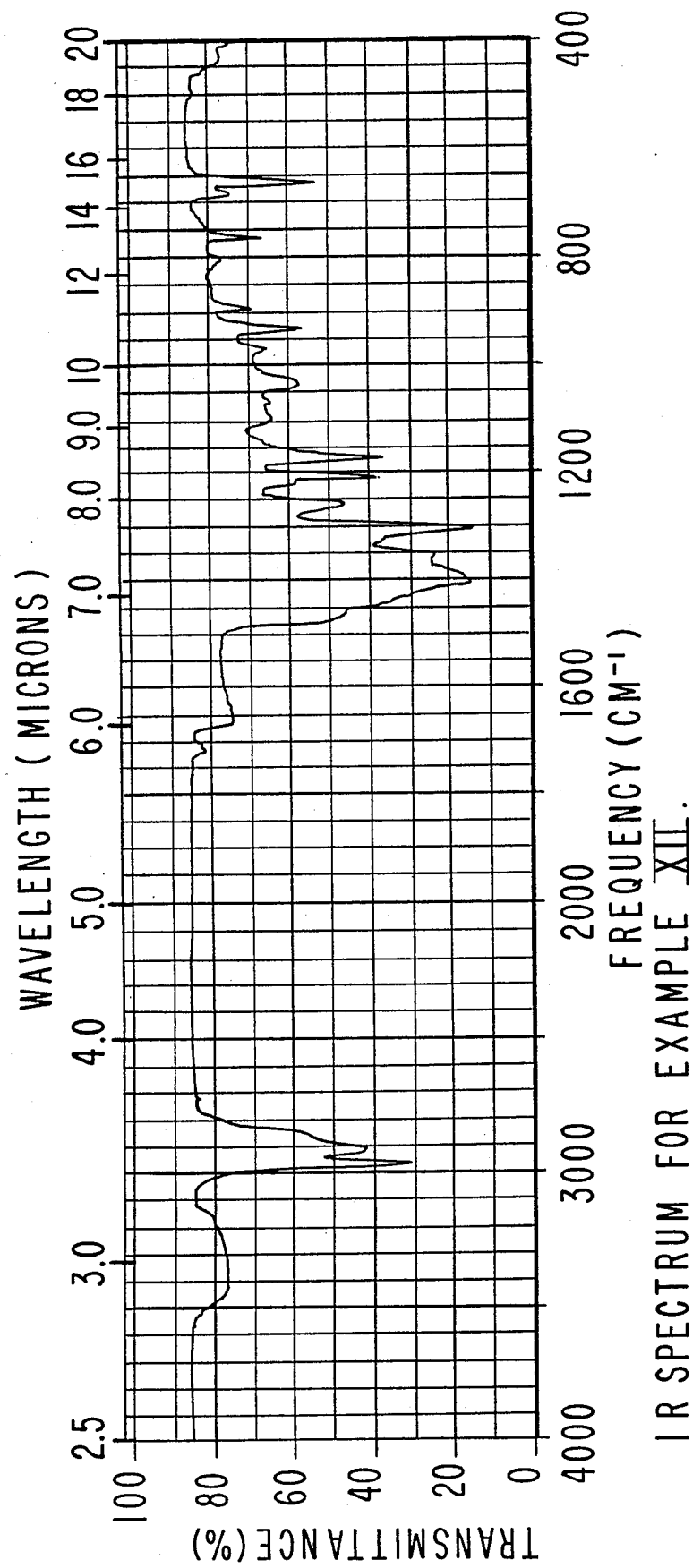

ARALKOXY, ALKOXY, ALKADIENYLOXY AND ALKENYLOXY-1,3,2-DIOXABORINANE DERIVATIVES AND USES THEREOF IN AUGMENTING OR ENHANCING THE AROMA OF PERFUME COMPOSITIONS, PERFUMED ARTICLES AND PERFUMED POLYMERS

BACKGROUND OF THE INVENTION

This invention relates to the aralkoxy, alkoxy, alkadienyloxy and alkenyloxy-1,3,2-dioxaborinane derivatives having the structure:

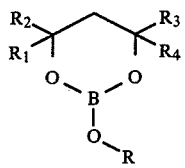

(wherein $R_1$, $R_2$, $R_3$ and $R_4$ are the same or different hydrogen, methyl and ethyl; and wherein R represents $C_6$ straight chain alkenyloxy; $C_{10}$ branched chain alkenyloxy; $C_{12}$ aralkoxy; $C_{12}$ branched chain alkoxy; or $C_{10}$ branched chain alkadienyloxy) and uses thereof in augmenting or enhancing the aroma of perfumed compositions including but not limited to drier-added fabric softener articles, fabric softener compositions and solid or liquid anionic, cationic, nonionic or zwitterionic detergents and perfumed polymers.

Materials which can provide various aromas, e.g., floral, rose, citrusy, muguet, fresh air, ozoney, woody, piney, camphoraceous, leafy and green aromas with muguet, rose, floral, citrusy, herbaceous, green, woody, peppery and straw-like undertones when contacted with water or water vapor are highly desirable in the art of perfumery and in the fabric softener and detergent art. Such substances in the past have not been commercially useful in view of the fact that residues of the aroma imparting substance are left on the articles to be perfumed or on the articles to be deodorized using such perfumery substances.

The use of boric acid esters in perfumery has heretofore not been disclosed in the prior art except for use as intermediates in the synthesis of chemicals useful in augmenting or enhancing the aroma of perfume compositions and perfumed articles.

Thus, the borate ester of 3-endo-methyl-3-exo(4'-methyl-5'-hydroxypentyl)norcamphor is shown as an intermediate for producing dihydro-beta-santalol in U.S. Pat. No. 3,662,007 issued on May 9, 1972.

However, arylalkanol esters of boric acid and glycol borates are shown to be useful for killing bacteria and fungi in U.S. Pat. No. 3,564,091 issued on Feb. 16, 1971. Indeed, the compound having the structure:

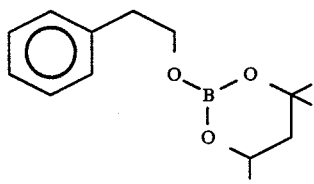

is shown to be useful in said U.S. Pat. No. 3,564,091 issued on Feb. 16, 1971 and the preparation of this compound is set forth at column 4, lines 35-48 of U.S. Pat. No. 3,564,091 the specification for which is incorporated by reference herein.

This compound is shown to be useful in the perfumery art in my copending application for U.S. Letters Patent, Ser. No. 073,289 filed on July 14, 1987.

The use as a precursor of the genus defined according to the structure:

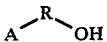

wherein A is an aryl hydrocarbon group of 5–14 carbon atoms and R is an aliphatic hydrocarbon group of more than one carbon atom and the compound:

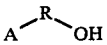

may be phenylethyl alcohol is set forth at lines 40–52, at column 1 of U.S. Pat. No. 3,564,091, to wit:

"More particularly, this invention relates to the use as biocides, compounds selected from the group consisting of (1) esters of boric acid and an alcohol of the formula A—R—OH, wherein A is an aryl hydrocarbon group of 5–14 carbon atoms and R is an aliphatic hydrocarbon group of more than one carbon atom, and (2) A—R—OH alcohol esters of glycol orthoborates wherein A and R are as described above.

In the general formula above, A is preferably selected from the group consisting of phenyl, naphthyl, phenanthracyl, and anthracyl. The glycol is selected from the group consisting of alpha and beta glycols containing 3–20 carbon atoms. The term boric acid embraces ortho-, meta-, and pyroboric acids, and boric oxide."

U.S. Pat. No. 2,839,564 issued on June 17, 1958; U.S. Pat. No. 2,940,839 issued on June 14, 1960; and U.S. Pat. No. 3,189,637 issued on June 15, 1965 as well as United Kingdom Patent Specification No. 722,538 published on Jan. 26, 1955 each disclose borate esters having the generic structure:

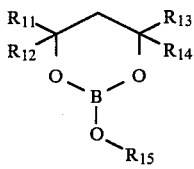

wherein $R_{11}$, $R_{12}$, $R_{13}$ and $R_{14}$ can represent hydrogen or alkyl and $R_{15}$ represent various hydrocarbon moieties (for example the definition of the R moieties at column 1, lines 29-34 of U.S. Pat. No. 2,839,564 states:

"wherein each R represents the same or different member of the group consisting of hydrogen and monovalent hydrocarbon radicals including alkyl, cycloalkyl, aryl, aralkyl and alkaryl groups, and R' represents a monovalent hydrocarbon radical including alkyl, cycloalkyl, aryl, aralkyl and alkaryl groups").

The borate esters having the generic structure:

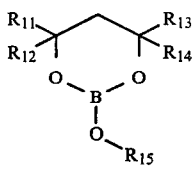

as disclosed in the aforementioned Patents and U.K. Patent Specification are indicated to be useful in causing fuel to be made more efficient on operation of internal combustion engines by reduction of octane requirements.

The prior art does not set forth explicitedly or implicitedly the use of such a genus or members of such a genus in perfumery or in perfumed articles or perfumed polymers.

U.S. Pat. No. 4,391,999 issued on July 5, 1983 entitled: "3,4,5,6,6-PENTAMETHYL HEXANOL-2- AND ALKYL HOMOLOGUES THEREOF; PROCESS FOR PREPARING SAME AND ORGANOLEPTIC USES THEREOF" on which I am the inventor, discloses the compound having the structure:

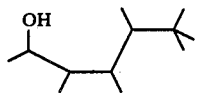

as being useful in augmenting or enhancing the aroma of perfumed compositions and perfumed articles.

The publication "Perfume and Flavor Chemicals (Aroma Chemicals)", Volume I, by Steffen Arctander (1969) discloses the usefulness of the compounds having the structure:

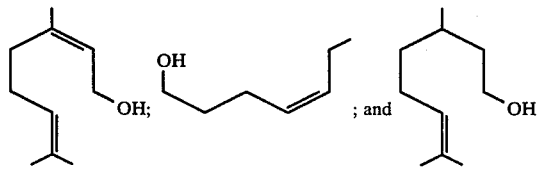

in augmenting or enhancing the aroma of perfume compositions at, inter alia, Monographs 1427 and 669.

Nothing in the prior art discloses the aralkoxy, alkoxy, alkadienyloxy and alkenyloxy-1,3,2-dioxaborinane derivatives defined according to the structure:

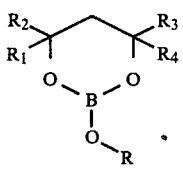

(wherein $R_1$, $R_2$, $R_3$ and $R_4$ are the same or different hydrogen, methyl and ethyl; and wherein R represents $C_6$ straight chain alkenyloxy; $C_{10}$ branched chain alkenyloxy; $C_{12}$ aralkoxy; $C_{12}$ branched chain alkoxy; or $C_{10}$ branched chain alkadienyloxy).

Furthermore, nothing in the prior art discloses the aralkoxy, alkoxy, alkadienyloxy and alkenyloxy-1,3,2-dioxaborinane derivatives generically as being useful in augmenting or enhancing the aroma of perfume compositions, perfumed articles and perfumed polymers.

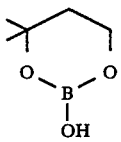

and citronellol having the structure:

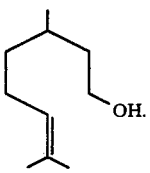

Figure 2:
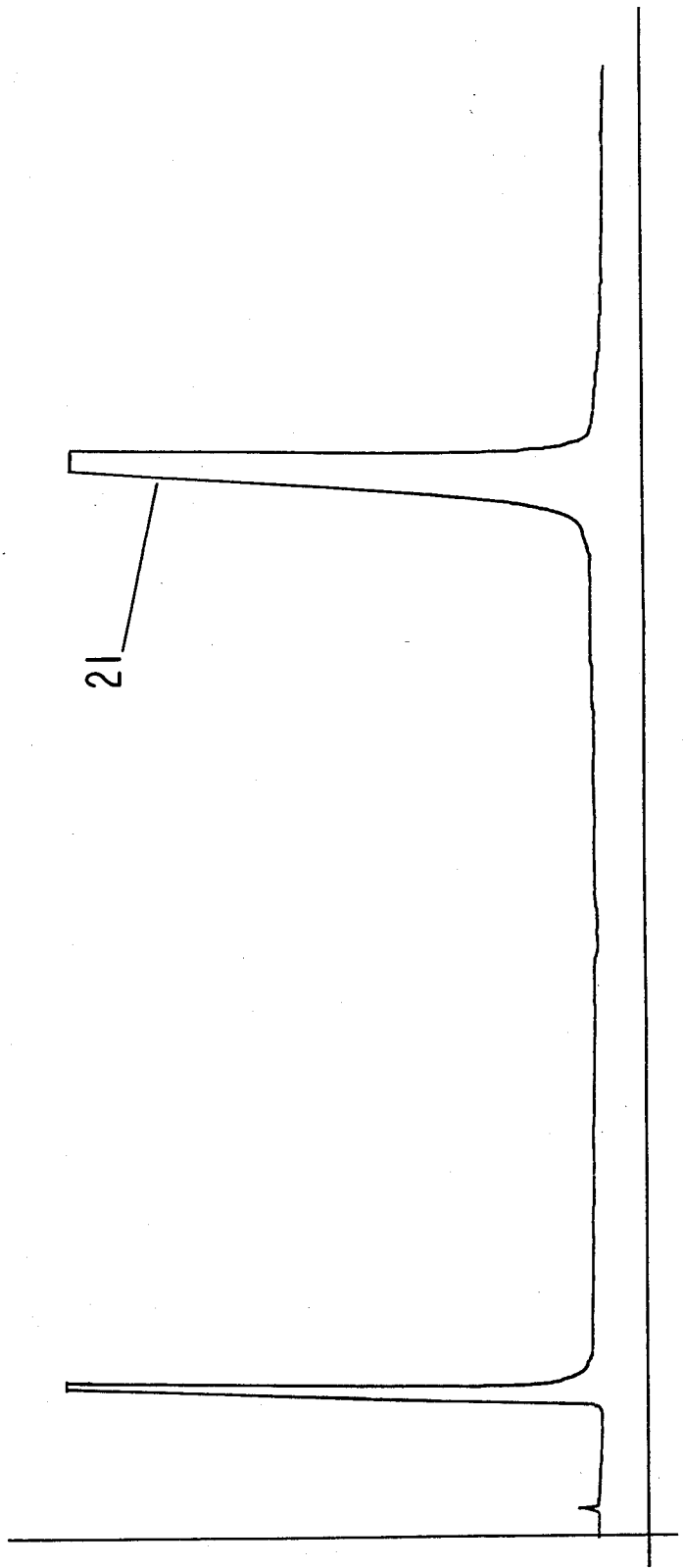

FIG. 2 is the GLC profile for the reaction product of Example II containing the compound having the structure:

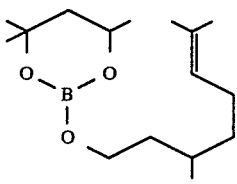

(2-(3,7-dimethyl-6-octenyloxy)-4,4,6-trimethyl-1,3,2-dioxaborinane) (Conditions: SE-30 column programmed at 100°–220° C. at 8° C. per minute).

Figure 3:
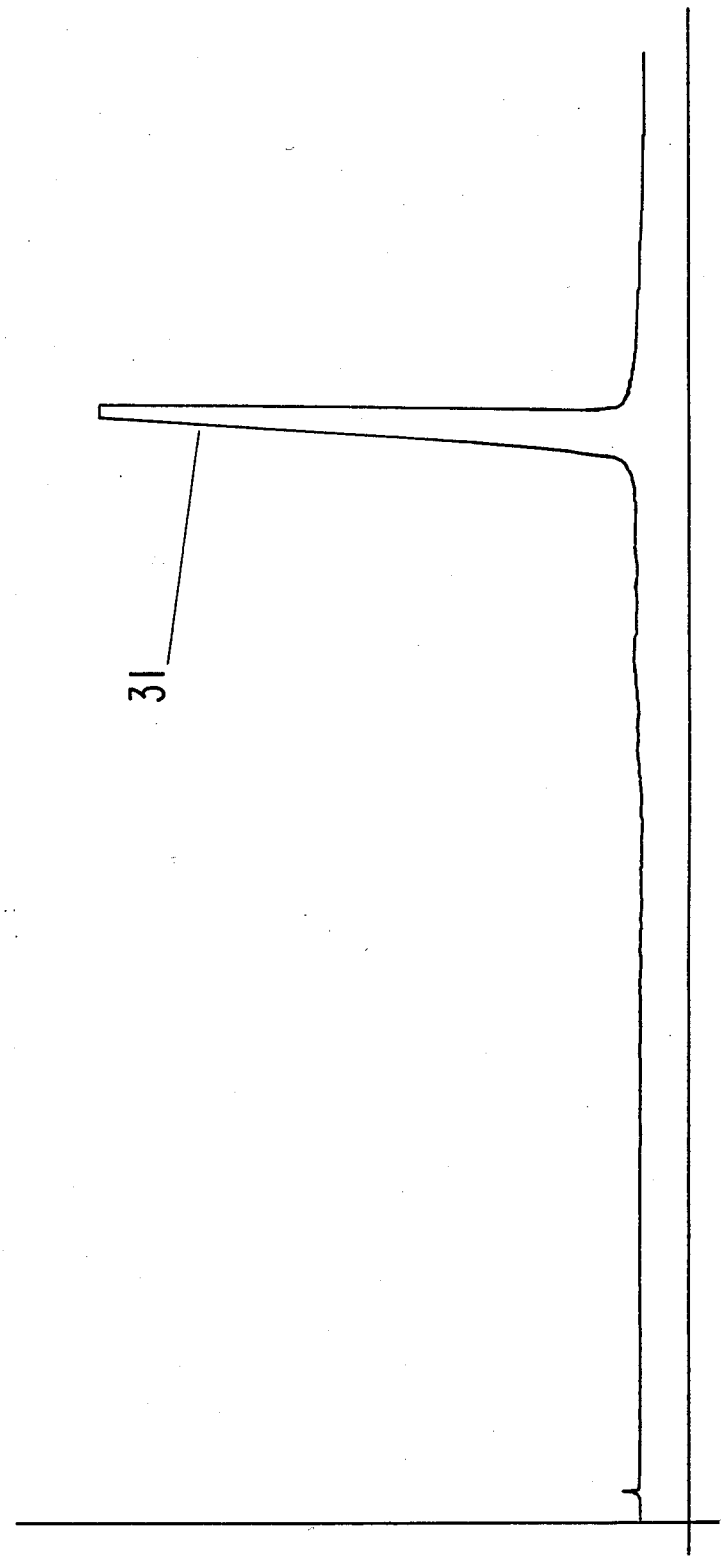

FIG. 3 is the GLC profile for bulked distillation fractions 3 and 4 of the reaction product of Example II containing the compound having the structure:

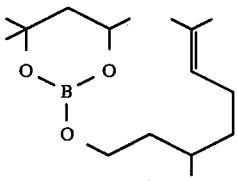

(Conditions: SE-30 column programmed at 100°–220° C. at 8° C. per minute).

Figure 4:
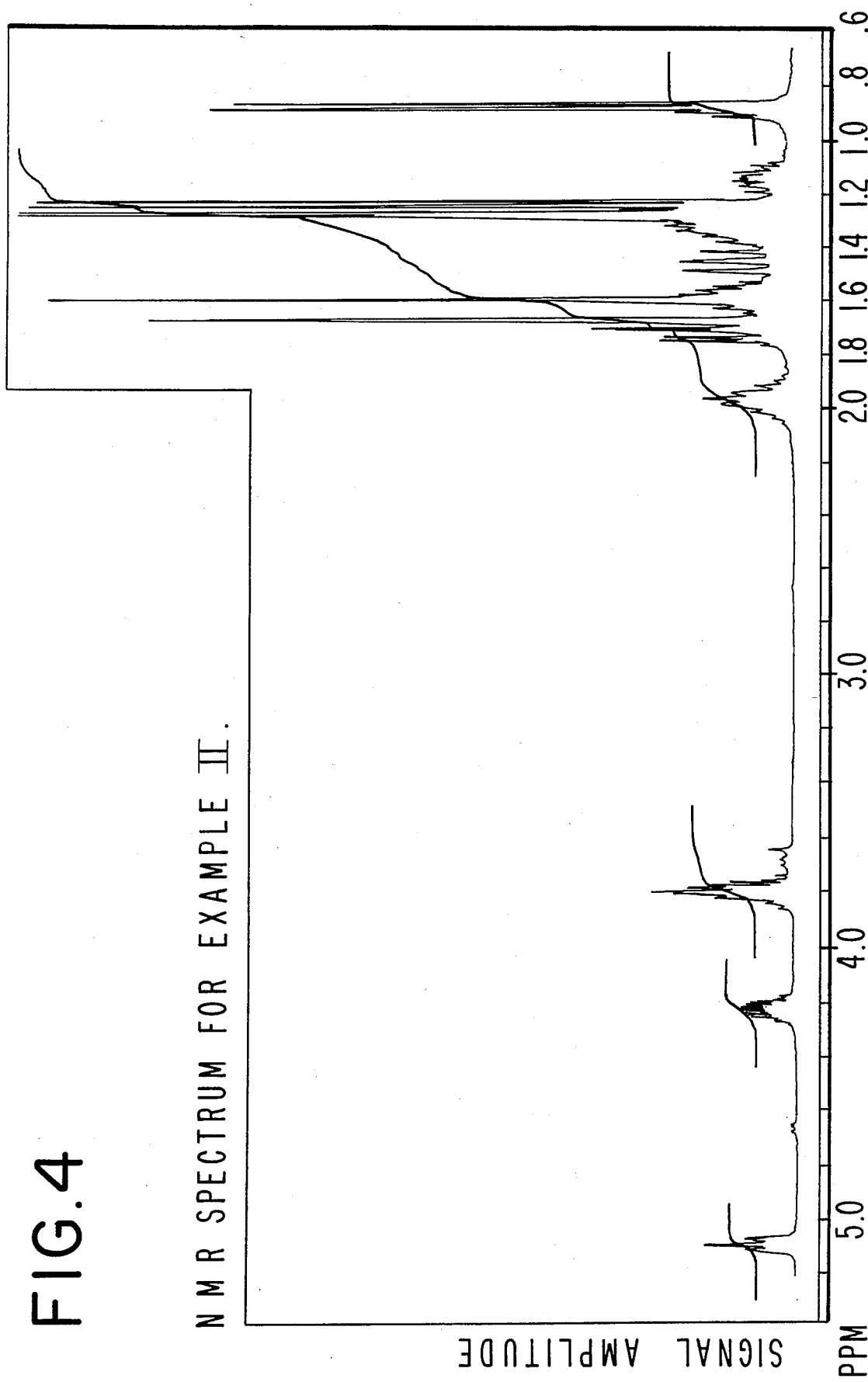

FIG. 4 is the NMR spectrum for the product of Example II having the structure:

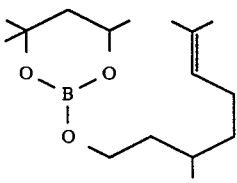

Figure 5:
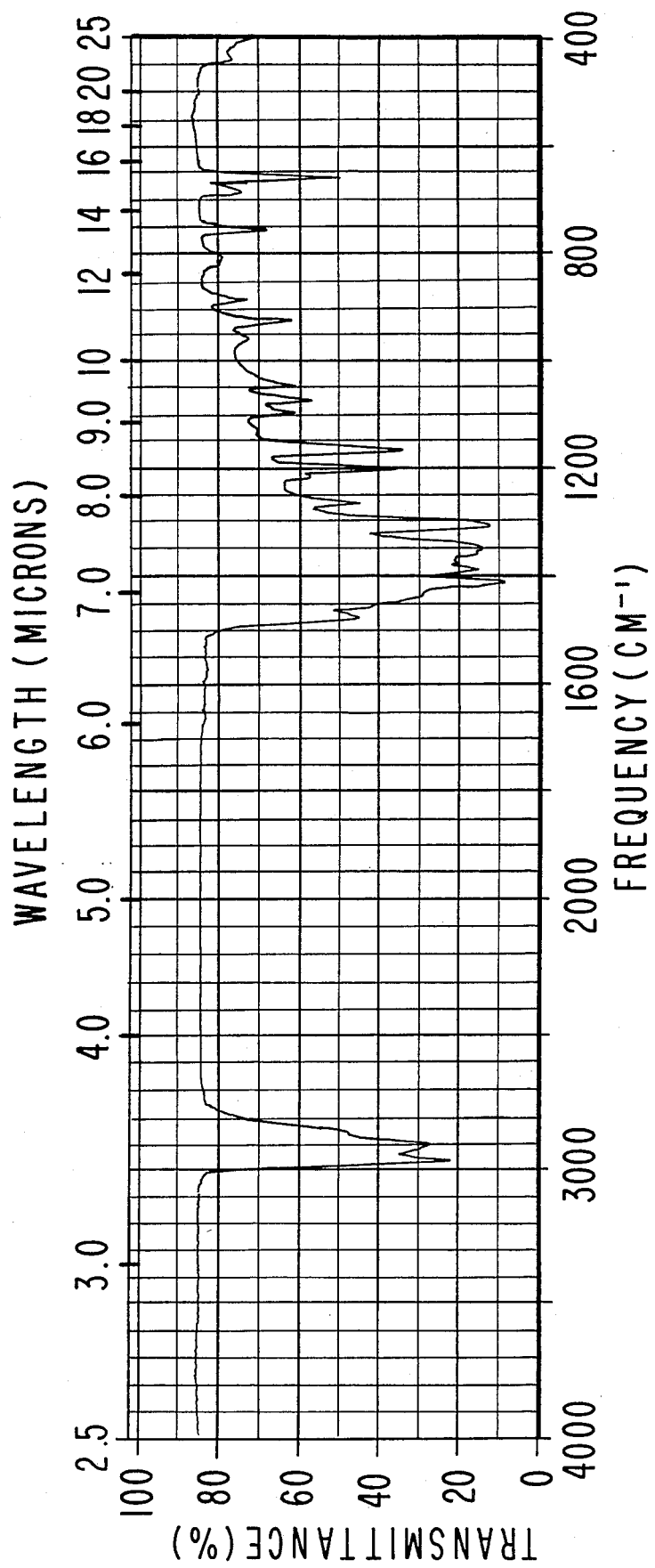

FIG. 5 is the infra-red spectrum for the compound having the structure:

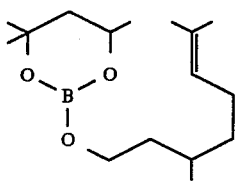

produced according to Example II.

Figure 6:
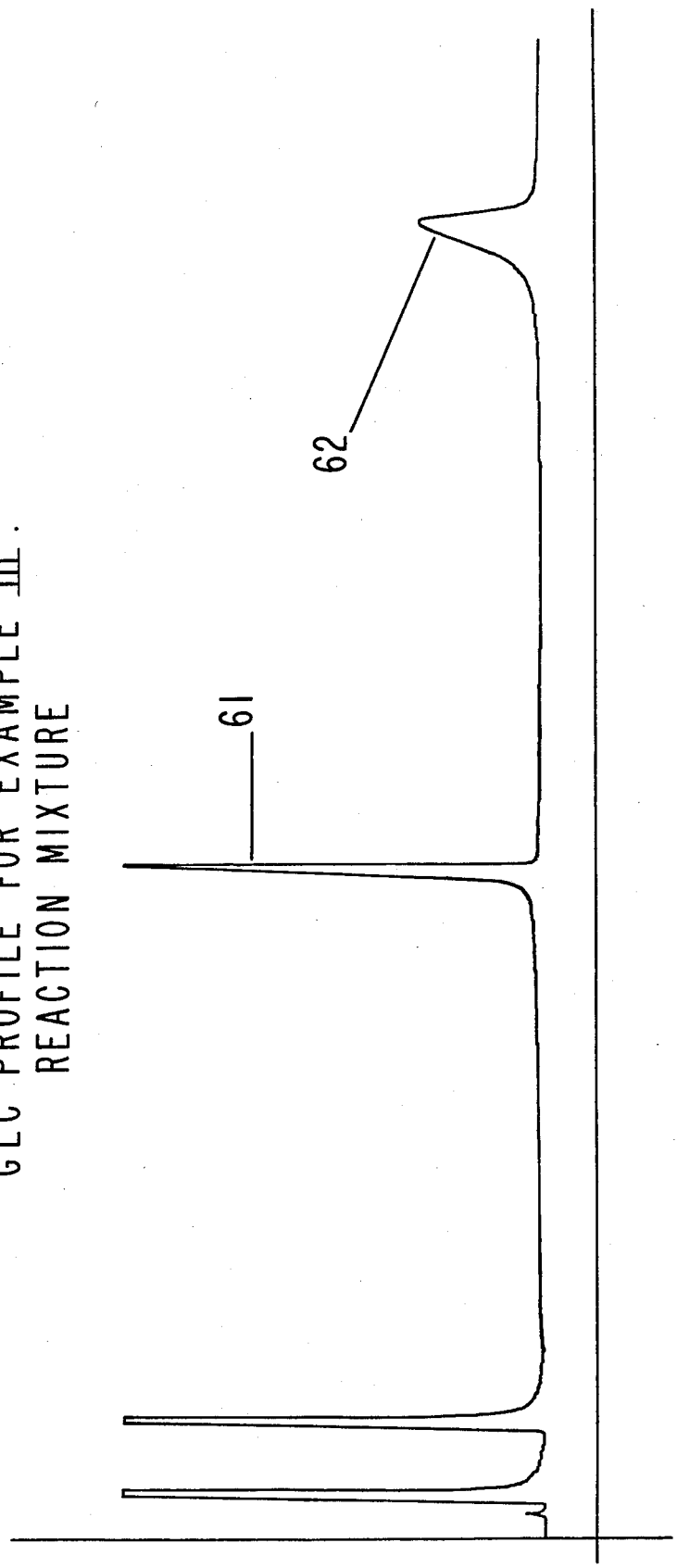

FIG. 6 is the GLC profile for the reaction mixture for Example III containing the compounds having the structures:

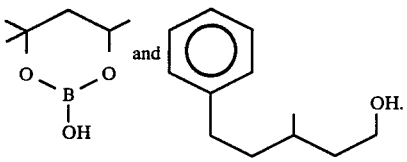

Figure 7:
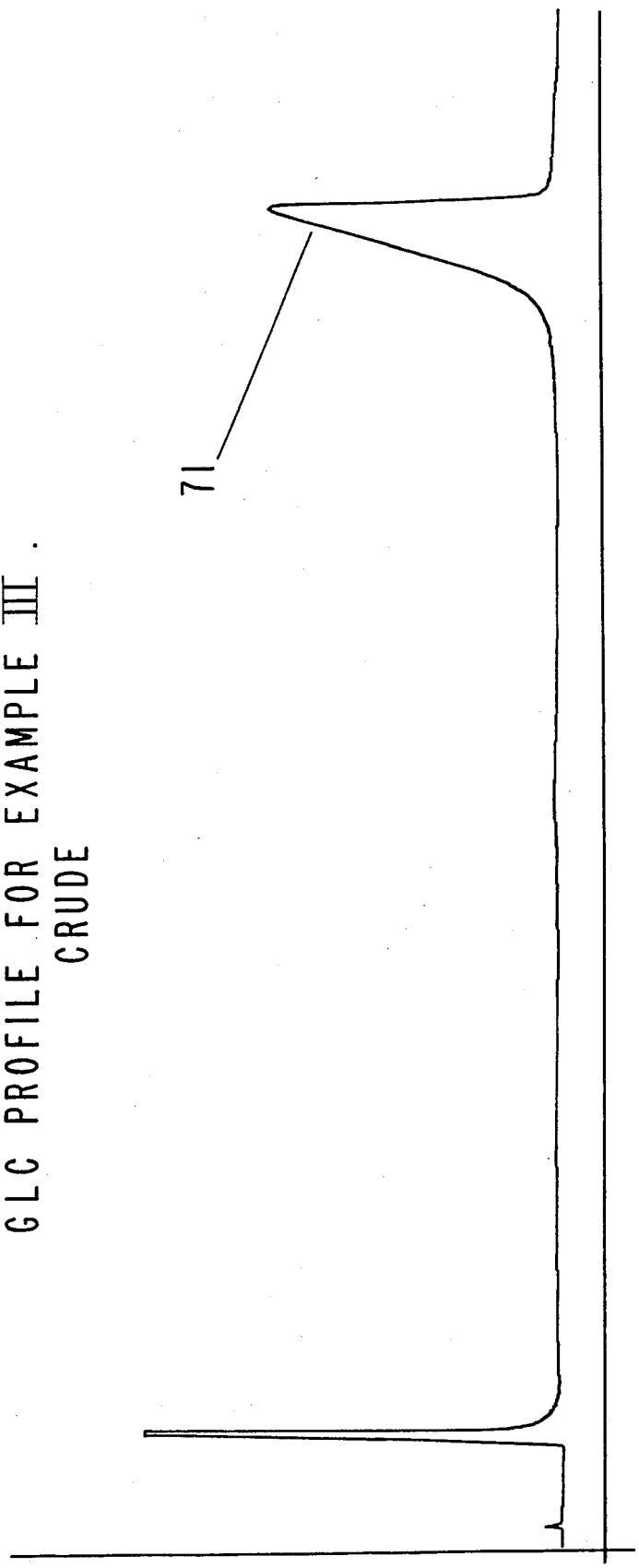

FIG. 7 is the GLC profile for the crude reaction product of Example III containing the compound having the structure:

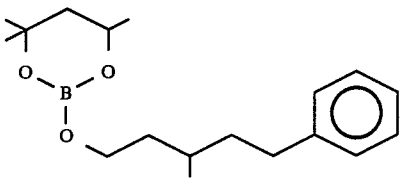

(2-(5-phenyl-3-methylpentyloxy)-4,4,6-trimethyl-1-3,2-dioxaborinane) (Conditions: SE-30 column programmed at 100°–220° C. at 8° C. per minute).

Figure 8:
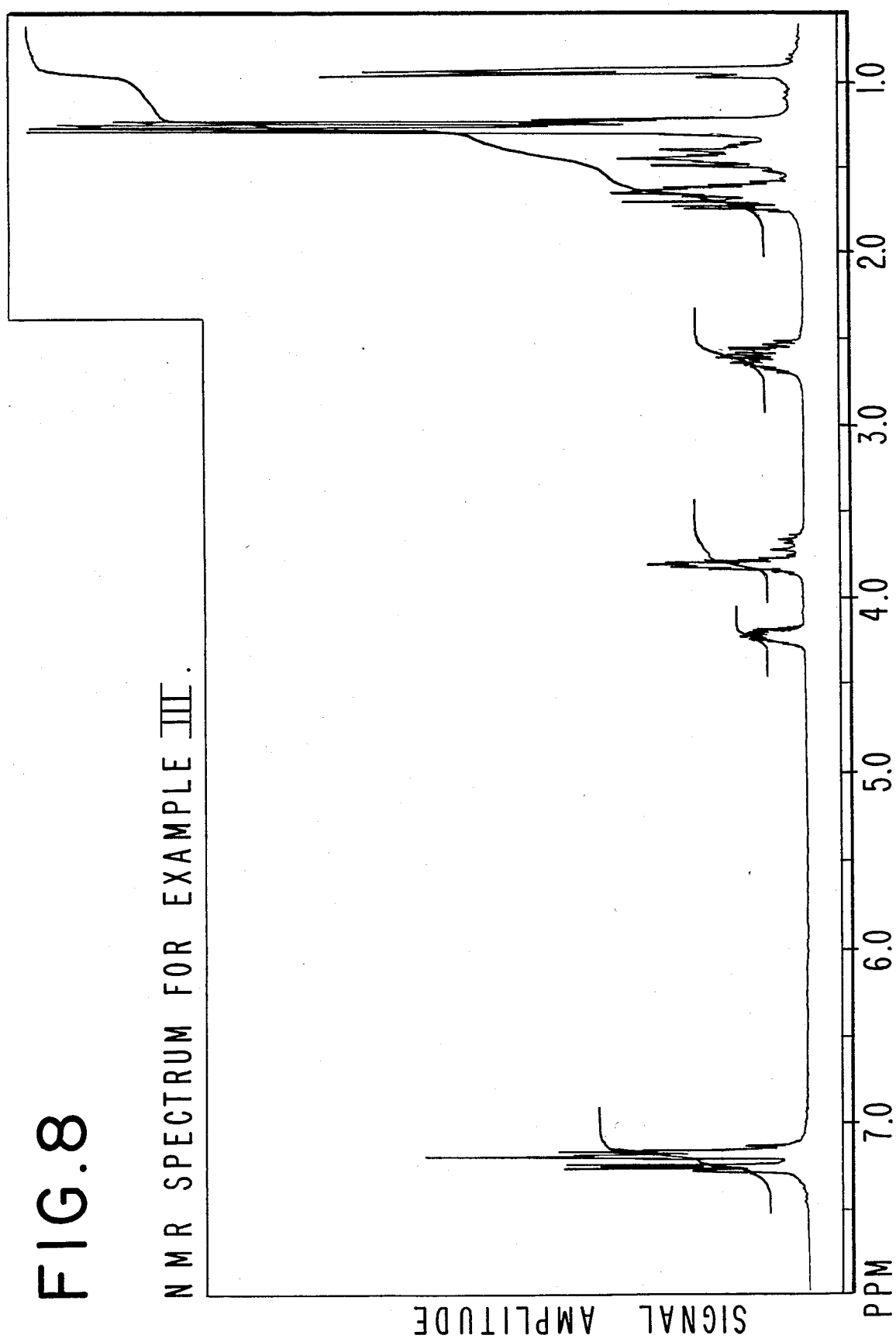

FIG. 8 is the NMR spectrum for the product of Example III containing the compound having the structure:

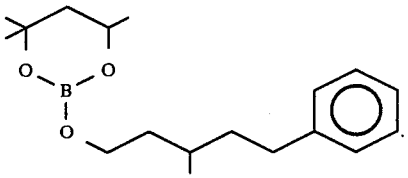

Figure 9:
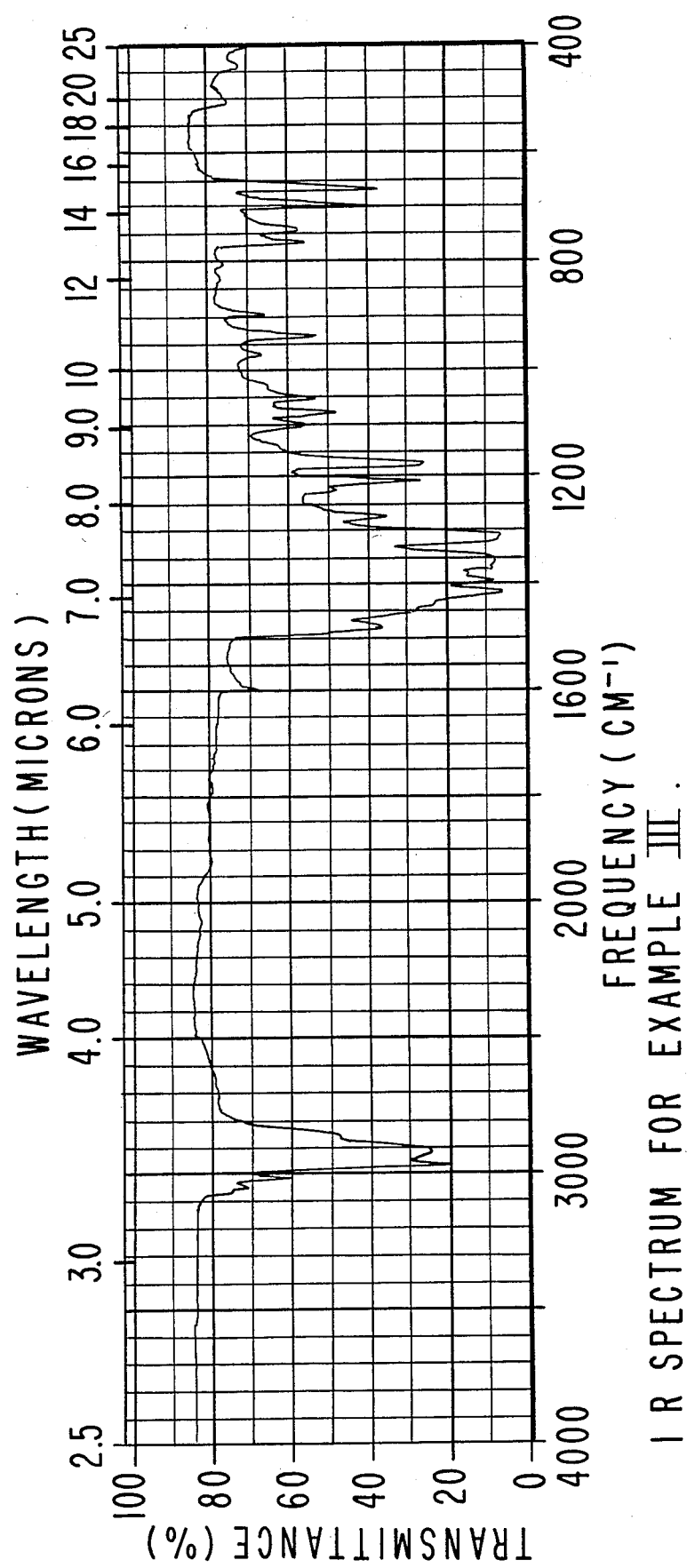

FIG. 9 is the infra-red spectrum for the compound having ths structure:

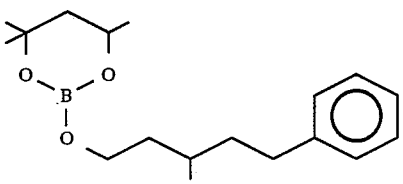

produced according to Example III.

Figure 10:
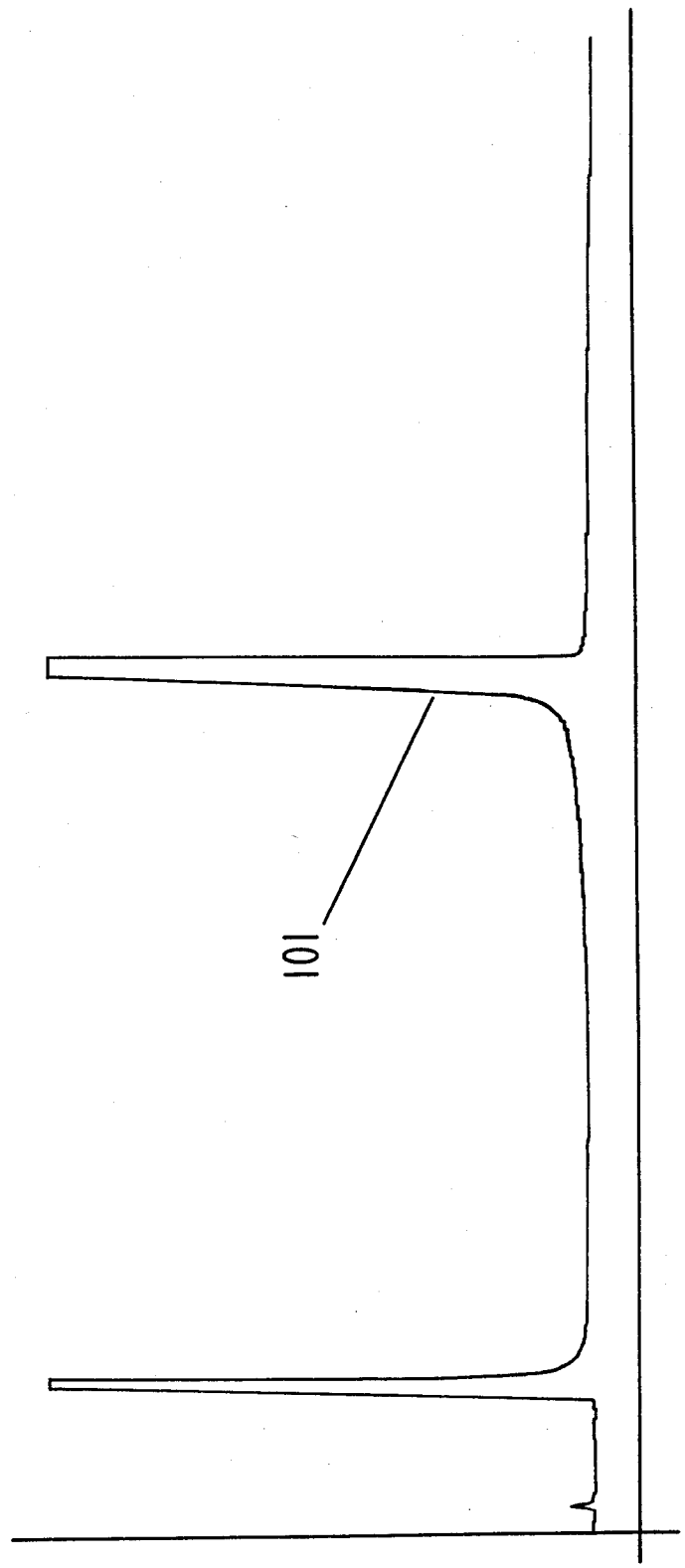

FIG. 10 is the GLC profile for the crude reaction product of Example IV containing the compounds having the structures:

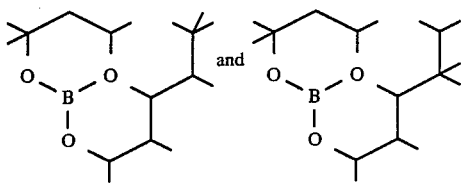

(2-(3,4,5,6,6-pentamethyl-2-heptyloxy)-4,4,6-trimethyl-1,3,2-dioxaborinane and 2-(3,4,5,5,6-pentamethyl-2-heptyloxy)-4,4,6-trimethyl-1,3,2-dioxaborinane).

Figure 11:
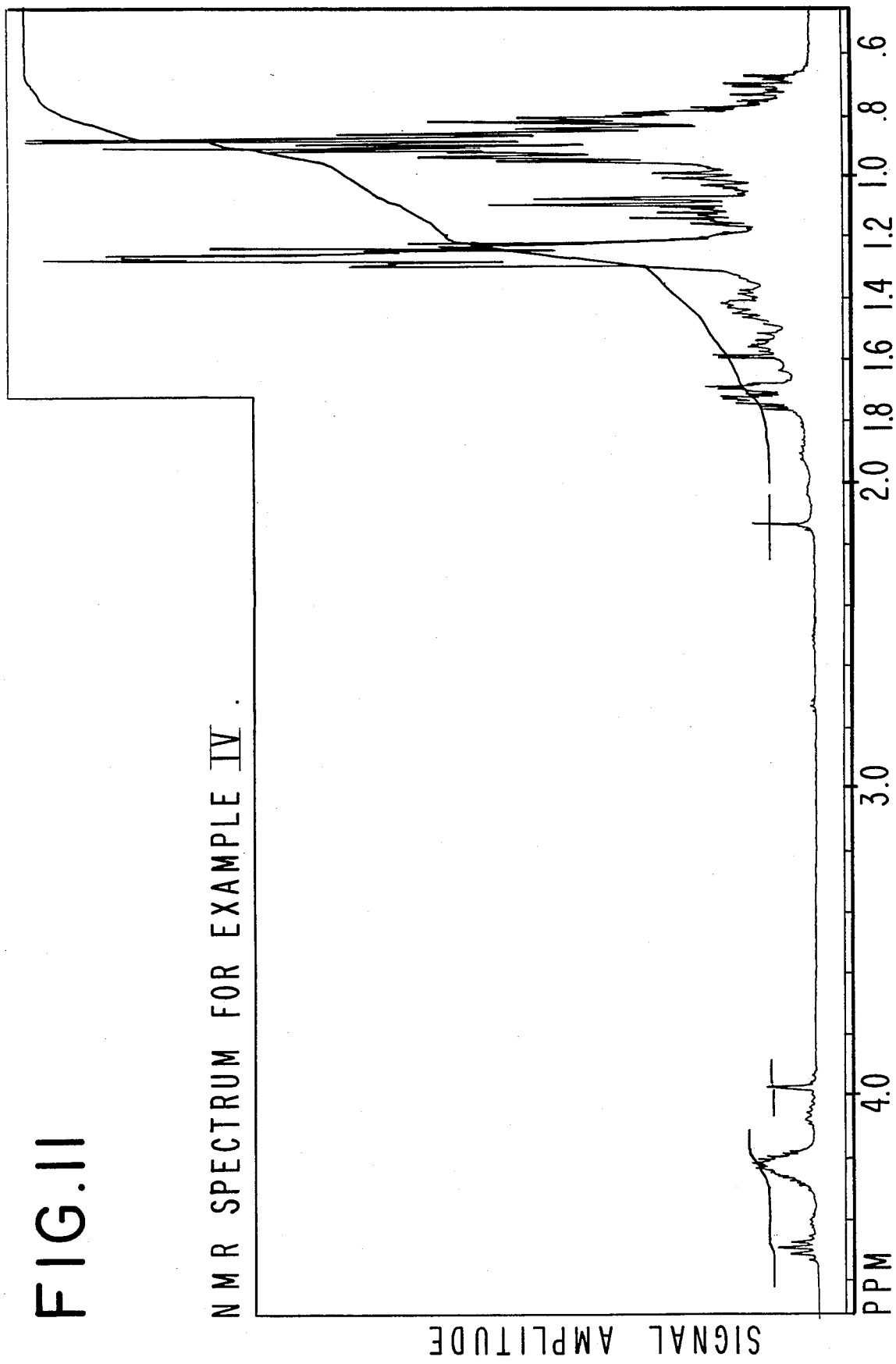

FIG. 11 is the NMR spectrum for the mixture of compounds having the structures:

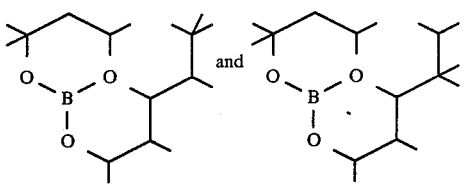

produced according to Example IV.

Figure 12:
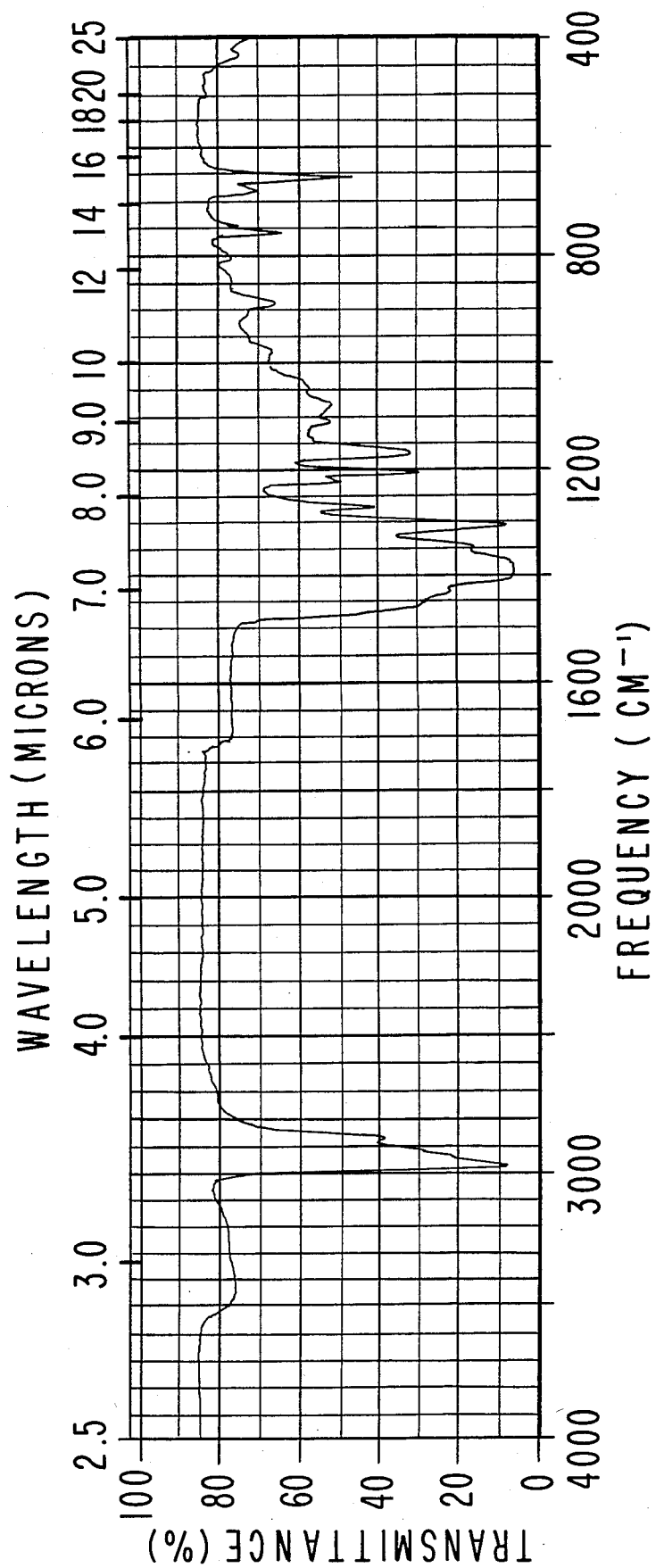

FIG. 12 is the infra-red spectrum for the mixture of compounds having the structures:

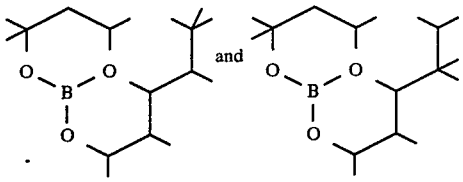

produced according to Example IV.

Figure 13:
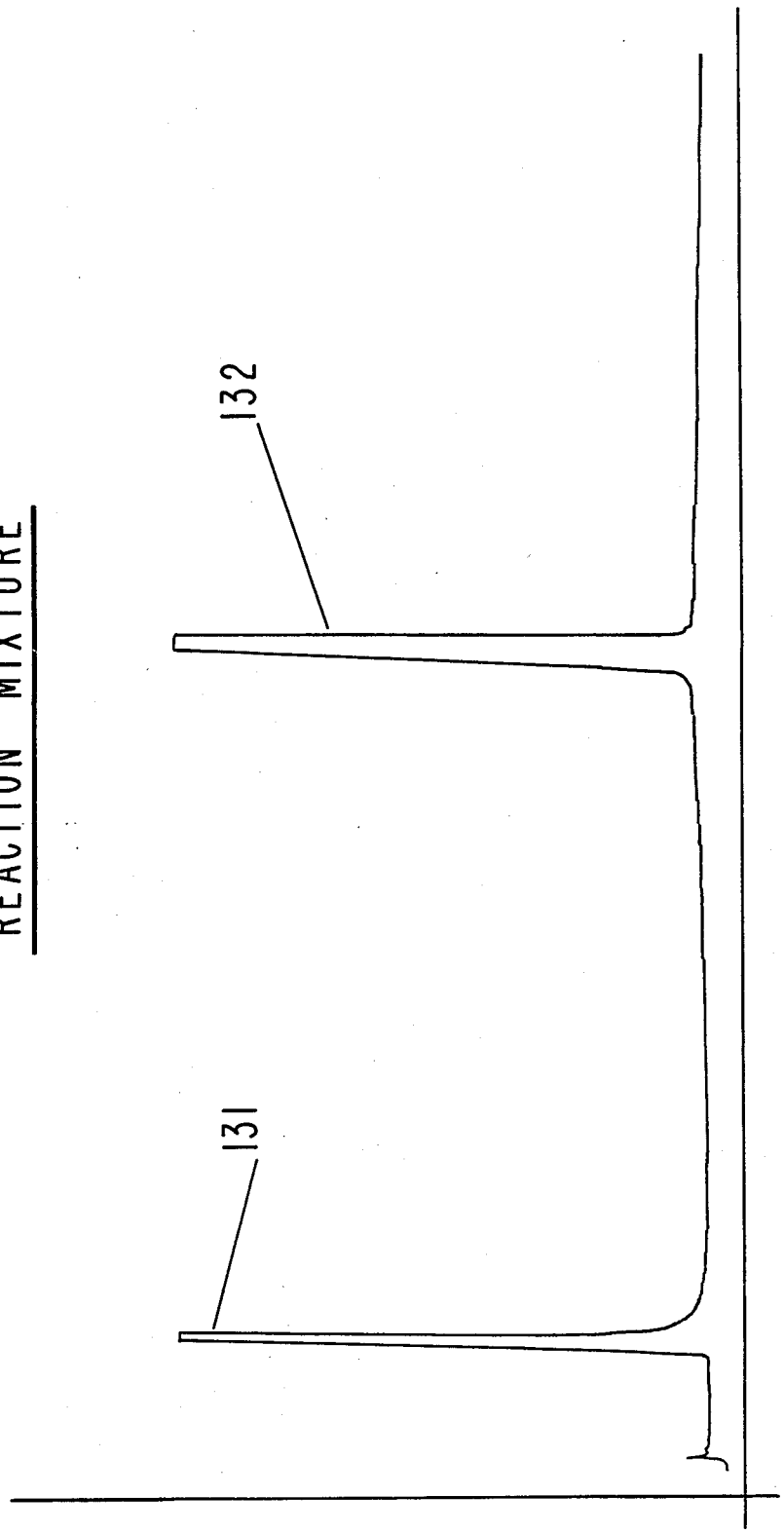

FIG. 13 is the GLC profile for the reaction mixture for carrying out the reaction of Example V containing the compounds having the structures:

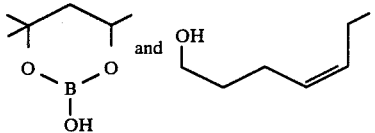

(Conditions: SE-30 column programmed at 100°–220° C. at 8° C. per minute).

Figure 14:
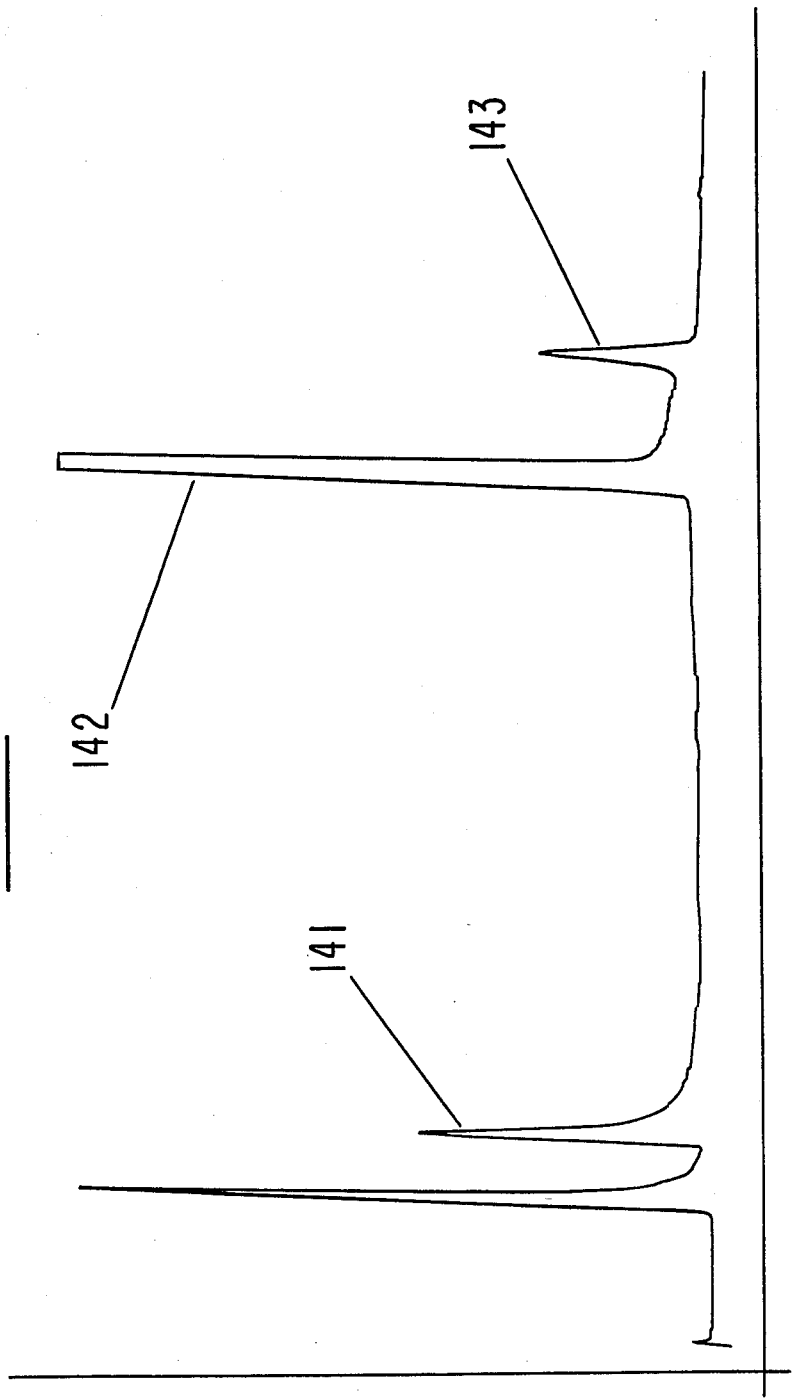

FIG. 14 is the GLC profile for the crude reaction product produced according to Example V containing the compound having the structure:

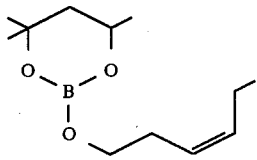

(2-[cis-3-hexenyloxy]-4,4,6-trimethyl-1,3,2-dioxaborinane) as well as cis-3-hexenol starting material having the structure:

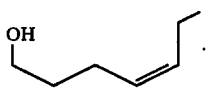

Figure 15:
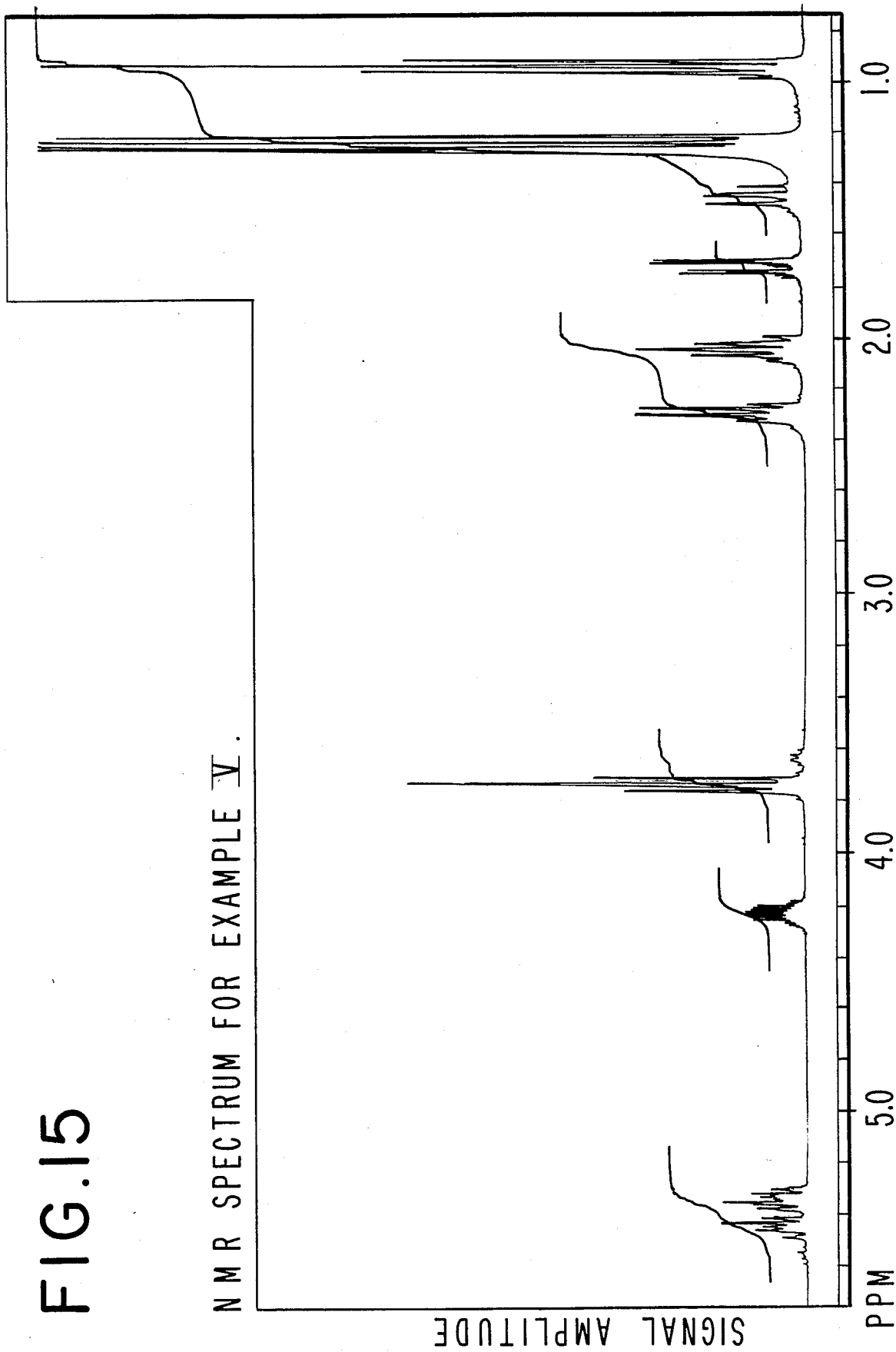

FIG. 15 is the NMR spectrum for the compound having the structure:

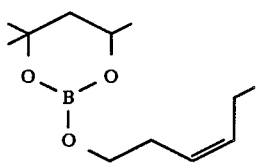

produced according to Example V.

Figure 16:
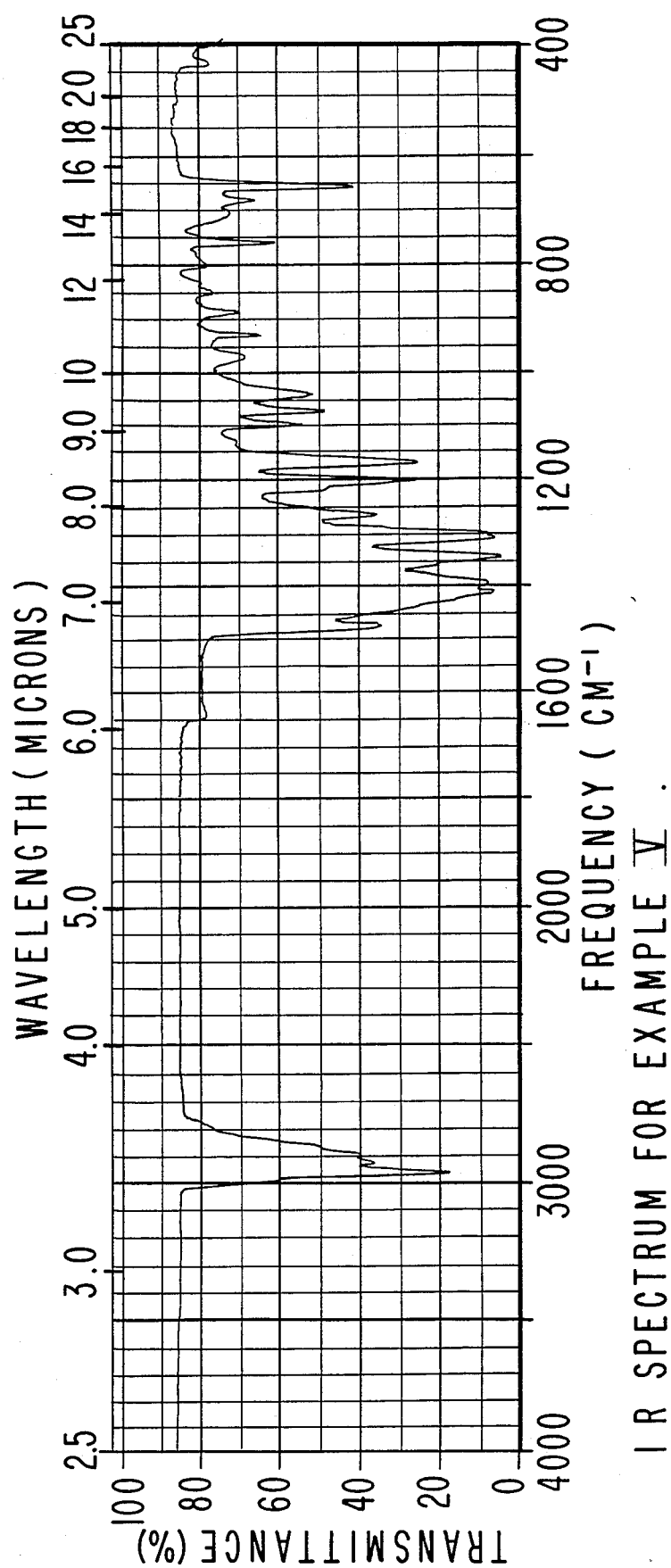

FIG. 16 is the infra-red spectrum for the compound having the structure:

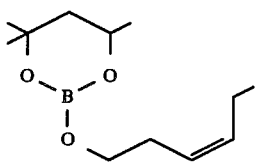

produced according to Example V.

FIG. 17 is a partial side elevation and partial sectional view of an apparatus for forming scented polymers using at least one of the aralkoxy, alkoxy, alkadienyloxy and alkenyloxy-1,3,2-dioxaborinane derivatives of my invention.

FIG. 18 is a section taken on line 18—18 of FIG. 17.

FIG. 19 is the GLC profile for the crude reaction product of Example XII containing the compound having the structure:

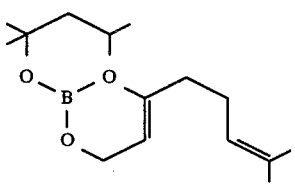

(Conditions: SE-30 column programmed at 100°-220° C. at 16° C. per minute).

FIG. 20 is the GLC profile for distillation fraction 13 of the reaction product of Example XII containing the compound having the structure:

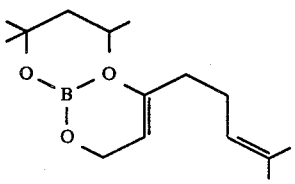

(Conditions: SE-30 column programmed at 100°-220° C. at 16° C. per minute).

FIG. 21 is the NMR spectrum for the compound having the structure:

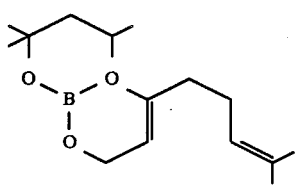

produced according to Example XII.

FIG. 22 is the infra-red spectrum for the compound having the structure:

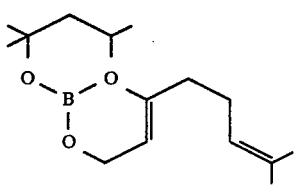

produced according to Example XII.

DETAILED DESCRIPTION OF THE DRAWINGS

Figure 1:
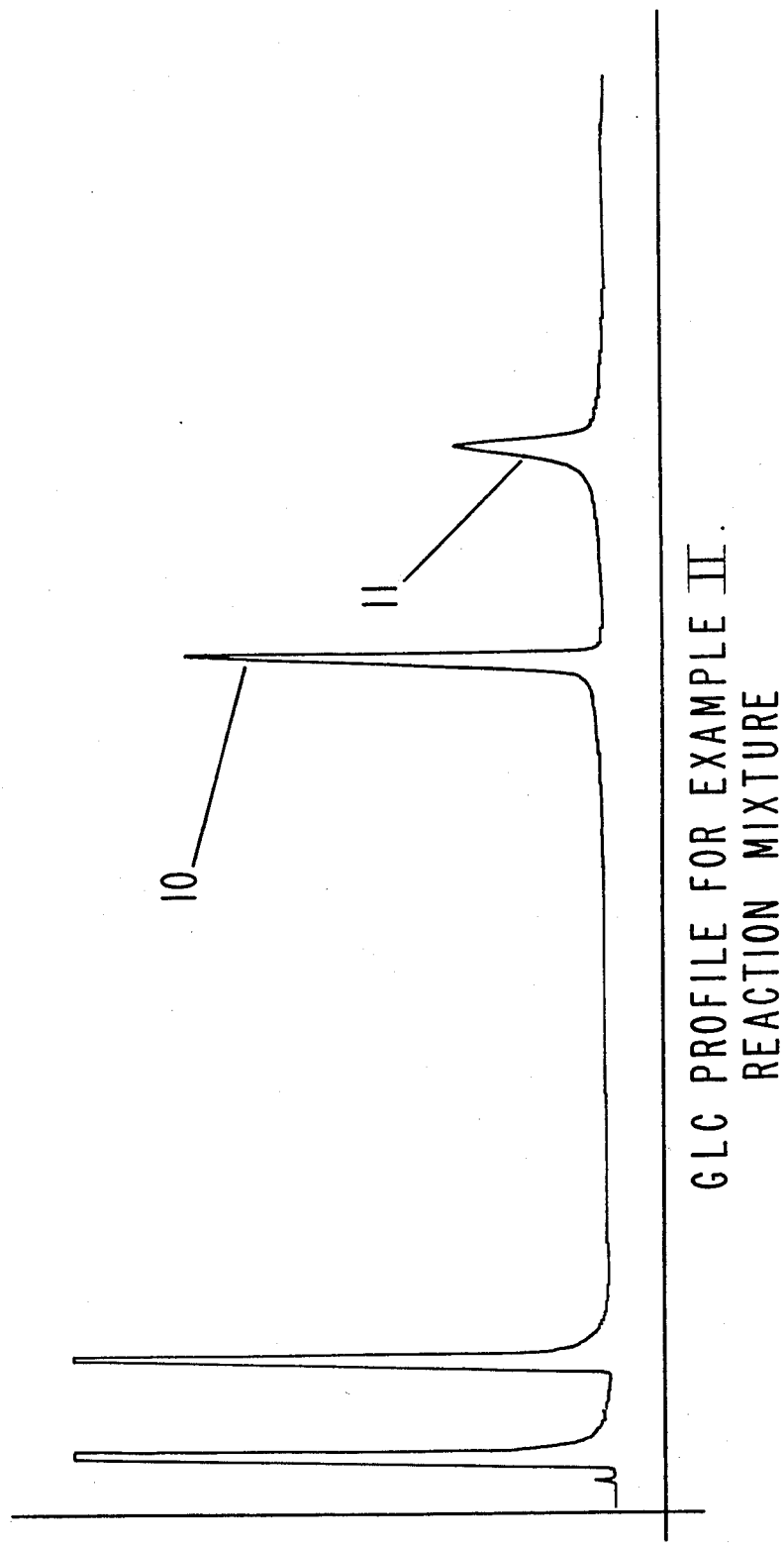
FIG. 1 is the GLC profile for the initial reaction mixture for Example II containing the compound having the structure.

In FIG. 1, the GLC profile for the reaction mixture for Example II, the peak indicated by reference numeral 10 is the peak for the compound having the structure:

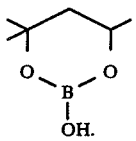

The peak indicated by reference numeral 11 is the peak for citronellol having the structure:

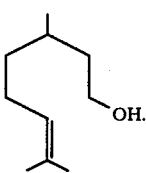

In FIG. 2, the GLC profile for the crude reaction product of Example II the peak indicated by reference numeral 21 is the peak for the compound having the structure:

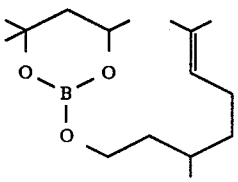

(2-[3,7-dimethyl-6-octenyloxy]-4,4,6-trimethyl-1,3,2-dioxaborinane).

In FIG. 3, the GLC profile for bulked fractions 3 and 4 of the reaction product of Example II, the peak indicated by reference numeral 31 is the peak for the compound having the structure:

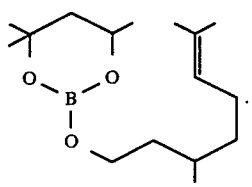

In FIG. 6, the GLC profile for the reaction mixture for the preparation of the reaction product of Example III, the peak indicated by reference numeral 61 is the peak for the compound having the structure:

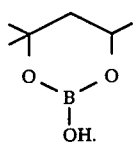

The peak indicated by reference numeral 62 is the peak for the compound having the structure:

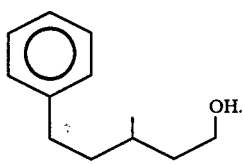

In FIG. 7, the GLC profile for the crude reaction product of Example III, the peak indicated by reference numeral 71 is the peak for the compound having the structure:

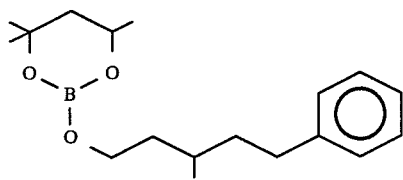

(2-[5-phenyl-3-methylpentyloxy]-4,4,6-trimethyl-1,3,2-dioxaborinane).

In FIG. 10, the GLC profile for the crude reaction product of Example IV, the peak indicated by reference numeral 101 is the peak for the mixture of compounds having the structures:

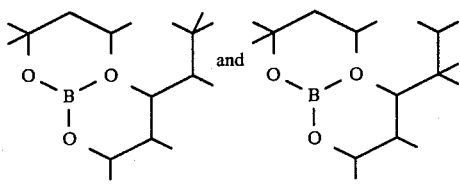

(2-[3,4,5,6,6-pentylmethyl-2-heptyloxy]-4,4,6-trimethyl-1,3,2-dioxaborinane and 2-[3,4,5,5,6-pentylmethyl-2-heptyloxy]-4,4,6-trimethyl-1,3,2-dioxaborinane).

In FIG. 13, the GLC profile for the reaction mixture for the preparation of the product of Example V, the peak indicated by reference numeral 131 is the peak for cis-3-hexenol having the structure:

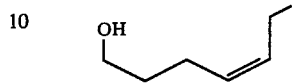

and the peak indicated by reference numeral 132 is the peak for the compound having the structure:

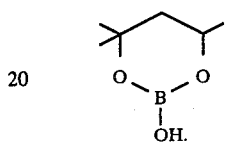

In FIG. 14, the GLC profile for the crude reaction product of Example V, the peak indicated by reference numeral 141 is the peak for cis-3-hexenol having the structure:

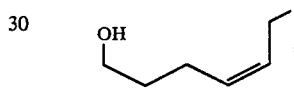

the peak indicated by reference numeral 142 is the peak for the reaction product having the structure:

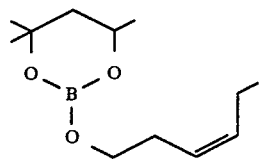

(2-[cis-3-hexenyloxy]-4,4,6-trimethyl-1,3,2-dioxaborinane); and the peak indicated by reference number 143 is the peak for the compound having the structure:

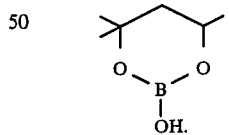

Referring to FIGS. 16 and 17, the invention embodied therein comprises a device for forming scented polymer pellets (e.g., polyethylene, polypropylene or mixtures such as polyepsiloncaprolactone and polyethylene or polypropylene or copolymers of polyvinyl acetate and polyethylene or the like) which comprises a vat or container 210 into which a polymer of mixture of polymers admixed with one of the aralkoxy, alkoxy, alkadienyloxy and alkenyloxy-1,3,2-dioxaborinane derivatives of my invention is placed.

The container is closed by an air-tight lid 228 clamped to the container by clamps 265. A stirrer 273 traverses the lid or cover 228 in air-tight manner and is rotated in a suitable manner. The surrounding cylinder 212 having heating coils which are supplied with electrical current through cable 214 from a rheostat or control 215 is operated to maintain the temperature inside the contaienr 210 such that the polymer such as polyethylene in the container will be maintained at a molten or liquid state. It has been found advantageous to employ a colorless, odorless polymer such as low density polyethylene with a viscosity ranging between about 180 and 220 centistokes and having a melting point in the neighborhood of 220° F. The heater 212 is operated to maintain the upper portion of the container 210 within the temperature range of from 250°–350° F. An additional bottom heater 218 is regulated through a control 220 connected thereto through a connecting wire 222 to maintain the lower portion of the container 210 within the temperature range of from 250°–350° F.

In accordance with this aspect of the invention, a polymer such as polyethylene or polypropylene is added to the container 210 and is then heated from 10 to 12 hours whereafter an aroma imparting material containing at least one of the aralkoxy, alkoxy, alkadienyloxy and alkenyloxy-1,3,2-dioxaborinane derivatives of my invention or at least one of the aralkoxy, alkoxy, alkadienyloxy and alkenyloxy-1,3,2-dioxaborinane derivatives of my invention per se is quickly added to the melt. The mixture containing one or more of the aralkoxy, alkoxy, alkadienyloxy and alkenyloxy-1,3,2-dioxaborinane derivatives of my invention must be compatible with the polymer and forms a homogeneous liquid melt therewith. The heat resisting mixture generally containing from 10–40% of at least one or more of the aralkoxy, alkoxy, alkadienyloxy and alkenyloxy-1,3,2-dioxaborinane derivatives of my invention or a mixture thereof is added to container 210; the mixture is stirred for a few minutes, for example, 5–15 minutes, and maintained within the temperature range as indicated previously by the heating coils 212 and 218 respectively. The controls 216 and 220 are connected through cables 224 and 226 through a suitable supply of electric current for supplying the power for heating purposes.

Thereafter, the valve "V" is opened permitting the mass to flow outwardly through a conduit 232 having a multiplicity of orifices 234 adjacent the lower side thereof. The outer end of the conduit 232 is closed so that the liquid polymer and at least one of the aralkoxy, alkoxy, alkadienyloxy and alkenyloxy-1,3,2-dioxaborinane derivatives of my invention or mixture containing same will continuously drop or drip through the orifices 234 downwardly from the conduit 232. During this time, the temperature of the polymer and the perfumant mixture containing at least one of the aralkoxy, alkoxy, alkadienyloxy and alkenyloxy-1,3,2-dioxaborinane derivatives of my invention in the container 210 is accurately controlled so that a temperature in the range of from 210° up to 275° F. will be maintained in the material exiting in the conduit 232. The regulation of the temperature through the control 216 and the control 220 is essential in order to insure temperature balance to provide for the continuous dropping or dripping of the molten polymer and the perfumant containing at least one of the aralkoxy, alkoxy, alkadienyloxy and alkenyloxy-1,3,2-dioxaborinane derivatives of my invention through the orifices 234 at a range which will insure the formation of droplets 236 which will fall downwardly onto a moving conveyor belt 238 trained to run between conveyor wheels 240 and 242 beneath the conduit 232. When the droplets 236 fall onto the conveyor belt 238 they form pellets 244 which harden almost instantaneously and fall off the end of the conveyor 238 into a container 246 which is advantageously filled with water or some other suitable liquid to insure the rapid cooling of each of the pellets. The pellets are then collected from the container 246 and packaged for shipment.

A feature of the invention is the provision for the moistening of the conveyor belt 238 to insure the rapid formation of the solid polymer-aromatizing agent containing pellets 244 without sticking to the belt. The belt 238 is advantageously of a material which will not normally stick to a melted polymer, but the moistening means 248 insures a sufficiently cold temperature of the belt surface for the adequate formation of the pellets 244. The moistening means comprises a container 250 which is continuously fed with water 252 to maintain a level 254 for moistening a sponge element 256 which bears against the exterior surface of the belt 238.

The resulting polymer can be described as a microporous polymer containing interconnected voids and filling said interconnected voids perfumery compositions containing substantial quantities of at least one of the aralkoxy, alkoxy, alkadienyloxy and alkenyloxy-1,3,2-dioxaborinane derivatives of my invention.

THE INVENTION

I have discovered that the genus of compounds having the structure:

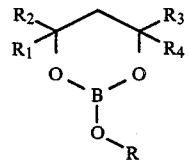

(wherein $R_1$, $R_2$, $R_3$ and $R_4$ are the same or different hydrogen, methyl and ethyl; and wherein R represents $C_6$ straight chain alkenyloxy; $C_{10}$ branched chain alkenyloxy; $C_{12}$ aralkoxy; $C_{12}$ branched chain alkoxy; or $C_{10}$ branched chain alkadienyloxy) can be used to augment or enhance or impart aroma in or to perfume compositions, colognes, perfumed polymers and perfumed articles including solid or liquid anionic, cationic, nonionic or zwitterionic detergents and fabric softener compositions and fabric softener articles including drier-added fabric softener articles as a result of hydrolysis of compounds having the generic structure:

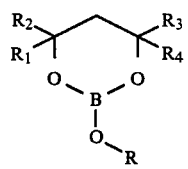

(wherein $R_1$, $R_2$, $R_3$ and $R_4$ are the same or different hydrogen, methyl and ethyl; and wherein R represents $C_6$ straight chain alkenyloxy; $C_{10}$ branched chain alkenyloxy; $C_{12}$ aralkoxy; $C_{12}$ branched chain alkoxy; or $C_{10}$ branched chain alkadienyloxy) taken alone or taken in admixture whereby substantially pure versions of compounds defined according to the structure:

R—OH are created subsequent to such hydrolysis according to the hydrolysis reaction:

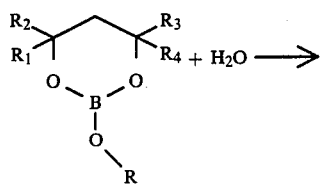

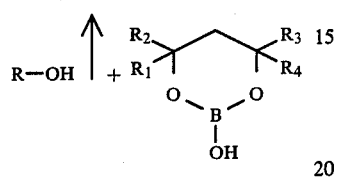

wherein R is as defined, supra.

The hydrolysis of members of the genus defined according to the structure:

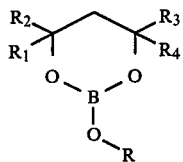

(wherein $R_1$, $R_2$, $R_3$ and $R_4$ are the same or different hydrogen, methyl and ethyl; and wherein R represents $C_6$ straight chain alkenyloxy; $C_{10}$ branched chain alkenyloxy; $C_{12}$ aralkoxy; $C_{12}$ branched chain alkoxy; or $C_{10}$ branched chain alkadienyloxy) takes place as a result of the utilization of the perfume composition, cologne, perfumed article or perfumed polymer, e.g., when another article with which the perfume composition, perfumed article, cologne or perfumed polymer is in contact is contacted with water or water vapor.

As a result of the hydrolysis of one or more compounds which is a member of the genus of compounds having the structure:

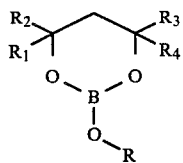

(wherein $R_1$, $R_2$, $R_3$ and $R_4$ are the same or different hydrogen, methyl and ethyl; and wherein R represents $C_6$ straight chain alkenyloxy; $C_{10}$ branched chain alkenyloxy; $C_{12}$ aralkoxy; $C_{12}$ branched chain alkoxy; or $C_{10}$ branched chain alkadienyloxy), one or more of the compounds of the genus:

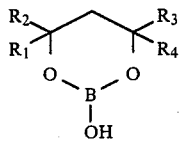

wherein $R_1$, $R_2$, $R_3$ and $R_4$ are defined, supra are formed and do not hydrolyze any further but are either washed away or volatize without causing any adverse reaction
  (i) with the article or composition or polymer to which the aroma is intended to be imparted; or
  (ii) to the user of the perfume composition or cologne.

By the same token the other hydrolysis product, namely the alcohol, to wit:

R—OH (wherein R is defined, supra) such as alcohols defined according to the structures:

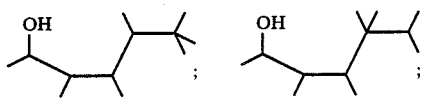

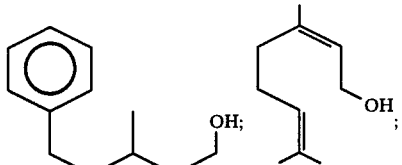

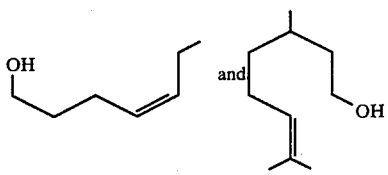

are also volatilized on use thereof without any adverse reaction to the article or polymer on which it (they) is (are) used or to the user of the perfume composition or cologne.

The compounds defined according to the generic structure:

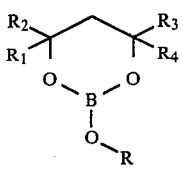

(wherein $R_1$, $R_2$, $R_3$ and $R_4$ are the same or different hydrogen, methyl and ethyl; and wherein R represents $C_6$ straight chain alkenyloxy; $C_{10}$ branched chain alkenyloxy; $C_{12}$ aralkoxy; $C_{12}$ branched chain alkoxy; or $C_{10}$ branched chain alkadienyloxy) are prepared by first reacting boric acid with a 1,3-glycol having the generic structure:

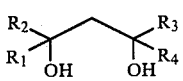

(wherein $R_1$, $R_2$, $R_3$ and $R_4$ are defined, supra (for example, the glycol having the structure:

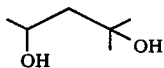

according to the reaction:

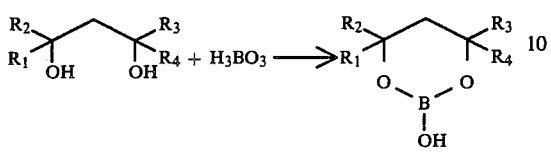

(wherein $R_1$, $R_2$, $R_3$ and $R_4$ are defined, supra) whereby a compound of the genus having the structure:

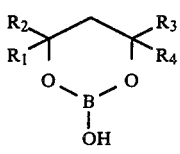

is formed).

The genus of compounds having the structure:

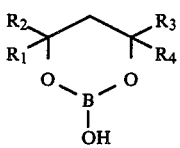

is then reacted with an alcohol having the structure:

, R—OH according to the reaction:

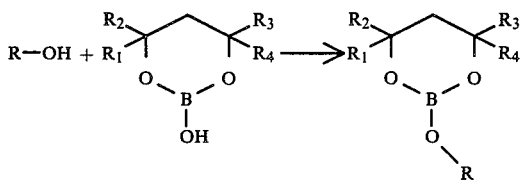

in order to form the genus of compounds defined according to the structure:

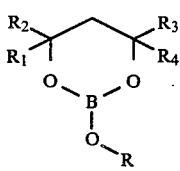

(wherein $R_1$, $R_2$, $R_3$ and $R_4$ are the same or different hydrogen, methyl and ethyl; and wherein R represents $C_6$ straight chain alkenyloxy; $C_{10}$ branched chain alkenyloxy; $C_{12}$ aralkoxy; $C_{12}$ branched chain alkoxy; or $C_{10}$ branched chain alkadienyloxy).

The mole ratio of boric acid:glycol having the structure:

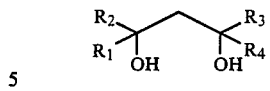

is approximately 1:1. The mole ratio of compound having the structure:

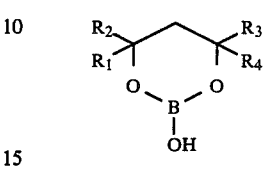

to alcohol having the structure:

R—OH is also approximately 1:1.

The first reaction, to wit:

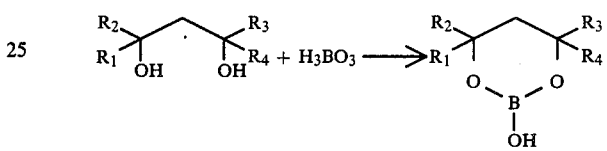

takes place in the presence of an inert solvent such as toluene. The concentration of glycol having the structure:

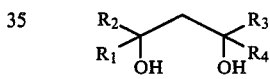

in the toluene is between 6 and 10 moles per liter of reaction mass.

The reaction takes place at approximately 110°–120° C. and water of reaction is constantly removed using, for example, a Dean Stark trap.

At the end of the reaction, the reaction mass is cooled and admixed with an alcohol defined according to the structure:

R—OH so that the reaction:

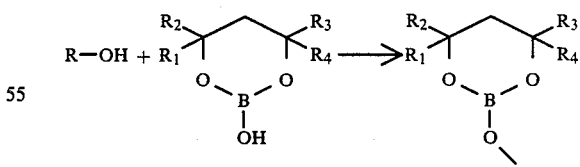

may proceed. This second reaction is carried out at reflux conditions at a temperature in the range of from about 70°–100° C. for a period of time of between 1 and about 5 hours until analysis indicates completion of the reaction (when all of the water of reaction is evolved).

The second reaction may be carried out in the absence of solvent or in the presence of an inert solvent such as cyclohexane or any other inert solvent having a boiling point which will enable the reaction to proceed in a reasonable period of time and yielding a reasonable yield of reaction product.

At the end of the reaction, the reaction mass is fractionally distilled. Indeed, an advantage of my invention is the fact that a member of the genus of compounds having the structure:

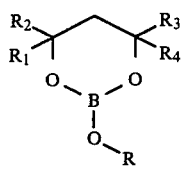

(wherein $R_1$, $R_2$, $R_3$ and $R_4$ are the same or different hydrogen, methyl and ethyl; and wherein R represents $C_6$ straight chain alkenyloxy; $C_{10}$ branched chain alkenyloxy; $C_{12}$ aralkoxy; $C_{12}$ branched chain alkoxy; or $C_{10}$ branched chain alkadienyloxy) is stable under all reaction conditions and is only decomposable in water; and then only decomposable into the alcohol having the structure:

R—OH and the compound having the structure:

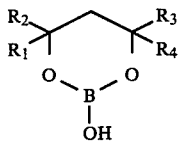

according to the reaction:

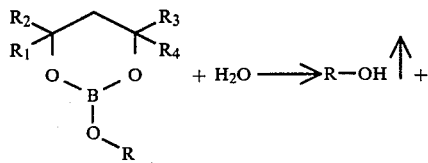

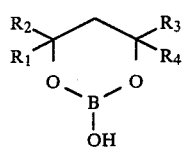

Other glycol borates are not so stable and are not so capable of being properly distilled and purified.

Table I below sets forth the chemical structure of several examples of aralkoxy, alkoxy, alkadienyloxy and alkenyloxy-1,3,2-dioxaborinane derivatives of my invention and each of their organoleptic properties:

TABLE I

| Structure of Aralkoxy, Alkoxy, Alkadienyloxy and Alkenyloxy-1,3,2-Dioxaborinane Derivatives | Organoleptic (Perfumery) Property |
|---|---|
| The compound having the structure: | A floral, rose, citrusy aroma profile with muguet and rose undertones. |
| produced according to Example II. | |
| The compound having the structure: produced according to Example III. | A rose, muguet and fresh air and ozoney aroma profile with floral, muguet, herbaceous, green and citrusy undertones. |
| Mixture of compounds having the structures: and prepared according to Example IV. | A woody, piney and camphoraceous aroma profile with woody, peppery and straw-like undertones. |
| The compound having the structure: prepared according to Example V. | A leafy, green aroma profile. |
| The compound having the structure: prepared according to Example XII. | A floral, rose aroma with rose undertones. |

The aralkoxy, alkoxy, alkadienyloxy and alkenyloxy-1,3,2-dioxaborinane derivatives of my invention can be used to contribute floral, rose, citrusy, muguet, fresh air, ozoney, woody, piney, camphoraceous, leafy and green aromas with muguet, rose, floral, citrusy, herbaceous, green, woody, peppery and straw-like undertones to perfume compositions, perfumed articles and colognes as a result of contact of same with water as stated, supra. Such perfumed articles are solid or liquid anionic, cationic, nonionic or zwitterionic detergents, perfumed polymers (with the polymers being water soluble), fabric softener compositions, fabric softener articles (e.g., BOUNCE ® a registered trademark of the Procter & Gamble Company of Cincinnati, Ohio), optical brighteners, fabric conditioners, hair preparations, shampoos and hair sprays. As olfactory agents the aralkoxy, alkoxy, alkadienyloxy and alkenyloxy-1,3,2-dioxaborinane derivatives of my invention can be formulated or used as components of a "perfume composition".

The term "perfume composition" is used herein to mean a mixture of organic compounds including, for example, alcohols, aldehydes, ketones, nitriles, ethers, lactones, esters other than the aralkoxy, alkoxy, alkadienyloxy and alkenyloxy-1,3,2-dioxaborinane derivatives of my invention and frequently, hydrocarbons which are admixed so that the combined odors of the individual components produce a pleasant or desired fragrance. Such perfume compositions usually contain: (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation and (d) top notes which are usually low-boiling, fresh-smelling materials.

In perfume compositions, the individual component will contribute its particular olfactory characteristics, but the overall effect of the perfume composition will be the sum of each of the effects of each of the ingredients. Thus, the individual compounds, the aralkoxy, alkoxy, alkadienyloxy and alkenyloxy-1,3,2-dioxaborinane derivatives of my invention or mixtures thereof can be used to alter the aroma characteristics of the perfume compositions (on contact with water or water vapor), for example, by highlighting or moderating the olfactory reaction contributed by another ingredient in the composition.

The amount of one or more of the aralkoxy, alkoxy, alkadienyloxy and alkenyloxy-1,3,2-dioxaborinane derivatives my invention which will be effective in perfume compositions depends upon many factors including the other ingredients, their amounts and the effects which are desired. It has been found that perfume compositions containing as little as 0.1% of the one or more of the aralkoxy, alkoxy, alkadienyloxy and alkenyloxy-1,3,2-dioxaborinane derivatives of my invention or even less and perfume compositions containing as much as 100% of one or more of the aralkoxy, alkoxy, alkadienyloxy and alkenyloxy-1,3,2-dioxaborinane derivatives of my invention can be used to impart interesting, floral, rose, citrusy, muguet, fresh-air, ozoney, woody, piney, camphoraceous, leafy and green aromas with muguet, rose, floral, citrusy, herbaceous, green, woody, peppery and straw-like undertones to perfumed articles, perfume compositions, perfumed polymers and colognes on contact with water as a result of hydrolysis.

Such perfumed articles include fabric softener compositions, drier-added fabric softener articles, cosmetic powders, talcs, solid or liquid anionic, cationic, nonionic or zwitterionic detergents and perfumed polymers. The amount employed can range up to 100% as stated, supra, and will depend on consideration of cost, nature of the end product and the effect desired on the finished product and particular fragrance sought.

Thus, one or more of the aralkoxy, alkoxy, alkadienyloxy and alkenyloxy-1,3,2-dioxaborinane derivatives of my invention, can be used alone or in a perfume composition as an olfactory component, in solid or liquid anionic, cationic, nonionic or zwitterionic detergents (including hand soaps) perfumed polymers (those which are microporous and those which are macroporous and contain particulate absorbent fillers such as talc), space odorants and deodorants; perfumes, colognes, toilet waters, bath salts, hair preparations such as lacquers, brilliantines, pomades and shampoos; cosmetic preparations such as creams, deodorants, hand lotions and sun screens; powders such as talcs, dusting powders, face powders and the like.

When used as an olfactory component of a perfumed article such as a microporous polymer or a macroporous polymer containing an absorbent filler or such as a solid or liquid anionic, cationic, nonionic or zwitterionic detergent or a cosmetic powder, as little as 0.01% of one or more of the aralkoxy, alkoxy, alkadienyloxy and alkenyloxy-1,3,2-dioxaborinane derivatives of my invention, (based on the perfumed article) will suffice to provide an interesting floral, rose, citrusy, muguet, fresh air, ozoney, woody, piney, camphoraceous, leafy or green aroma profile with muguet, rose, floral, citrusy, herbaceous, green, woody, peppery and/or straw-like undertones. Generally, no more than 0.8% of one or more of the aralkoxy, alkoxy, alkadienyloxy and alkenyloxy-1,3,2-dioxaborinane derivatives of my invention is required. Thus, the range of one or more of the aralkoxy, alkoxy, alkadienyloxy and alkenyloxy-1,3,2-dioxaborinane derivatives of my invention in perfumed articles may vary from about 0.01% up to about 0.8%. On the other hand, when used in perfumed polymers the aralkoxy, alkadienyloxy and alkenyloxy-1,3,2-dioxaborinane derivatives of my invention can be loaded into the polymers up to an amount of approximately 60% or be as little as 0.01%.

In addition, the perfume compositions of my invention can contain a vehicle or carrier for one or more of the aralkoxy, alkoxy, alkadienyloxy and alkenyloxy-1,3,2-dioxaborinane derivatives of my invention alone or with other ingredients. The vehicle can be a liquid such as an alcohol such as ethanol, a glycol such as propylene glycol or the like. The carrier can be an absorbent solid such as a gum (e.g., xanthan gum or gum arabic) or components for encapsulating the composition as by coacervation using gelatin or by forming a polymeric shell around a liquid perfume center by means of the use of a urea formaldehyde prepolymer.

The following Example I sets forth a process for preparing the precursor having the structure:

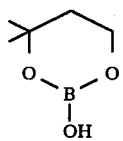

of the materials formed using Examples II, III, IV and V. The following Examples II, III, IV and V set forth processes for preparing the aralkoxy, alkoxy, alkadienyloxy and alkenyloxy-1,3,2-dioxaborinane derivatives of my invention. Examples following Example V set forth methods for using the aralkoxy, alkoxy, alkadienyloxy and alkenyloxy-1,3,2-dioxaborinane derivatives of my invention for their organoleptic properties.

Unless otherwise indicated, all parts and percentages are by weight.

EXAMPLE I

PREPARATION OF 4,4,6-TRIMETHYL-1,3,2-DIOXABORINANE

Reaction:

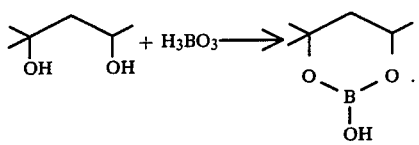

Into a 3 liter reaction vessel equipped with stirrer, thermometer, reflux condenser and Dean Stark trap is placed 710.0 grams of 2-methyl-2,4-pentanediol; 372.0 grams of boric acid and 500 grams of toluene. With stirring the reaction mass is heated to 87° C. and, by way of the Dean Stark trap water is eliminated and the alcohol having the structure:

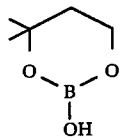

is recovered. The reaction temperature gradually rises to 125° C. as water is eliminated and the total reaction time is 10 hours. The total amount of water evolved is 252.0 grams. When the water of reaction ceases to evolve, the reaction mass is cooled to 70° C. Once all of the water is removed the compound having the structure:

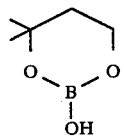

as recovered weighs 1227.0 grams. This material having the structure:

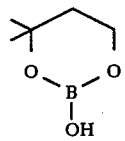

is used for Examples II, III, IV and V, infra.

EXAMPLE II

PREPARATION OF 2-(3,7-DIMETHYL-6-OCTENYLOXY)-4,4,6-TRIMETHYL-1,3,2-DIOXABORINANE

Reaction:

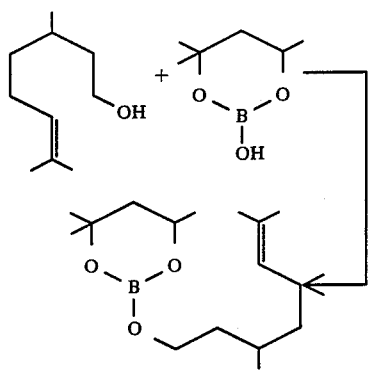

409.0 Grams of the compound having the structure:

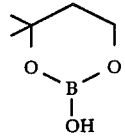

produced according to Example II is placed into a 1 liter reaction vessel equipped with stirrer, thermometer, reflux condenser and heating mantle. 312.2 Grams of citronellol having the structure:

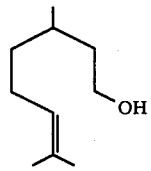

is slowly fed into the reaction vessel. The reaction mass is then heated to 92°-94° C. and maintained at that temperature with stirring for a period of three hours. At the end of the three hour period, the reaction mass is distilled on a 4" splash column yielding the following fractions:

| Fraction No. | Vapor Temp. (°C.) | Liquid Temp. (°C.) | Vacuum mm/Hg. Pressure |
|---|---|---|---|
| 1 | 115/134 | 156/145 | 3.0 |
| 2 | 135 | 146 | 3.0 |
| 3 | 136 | 146 | 3.0 |
| 4 | 136 | 149 | 3.0 |
| 5 | 138 | 158 | 3.0 |

Fractions 3 and 4 (136° C. and 3 mm/Hg. pressure) are bulked yielding the product having the structure:

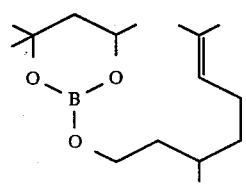

This product has a floral, rose and citrusy aroma with a muguet and rose undertone.

FIG. 1 is the GLC profile for the reaction mixture prior to the reaction. The peak indicated by reference numeral 10 is the peak for the compound having the structure:

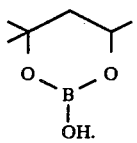

The peak indicated by reference numeral 11 is the peak for citronellol having the structure:

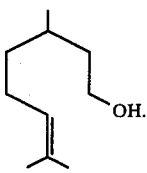

FIG. 2 is the GLC profile for the crude reaction product. The peak indicated by reference numeral 21 is the peak for the product having the structure:

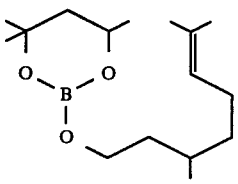

(Conditions: SE-30 column programmed at 100°-220° C. at 8° C. per minute).

FIG. 3 is the GLC profile for bulked fractions 3 and 4 for the compound having the structure:

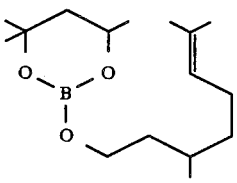

(Conditions: SE-30 column programmed at 100°-220° C. at 8° C. per minute).

FIG. 4 is the NMR spectrum for the compound having the structure:

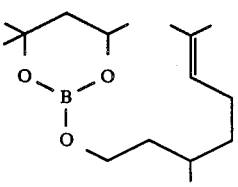

FIG. 5 is the infra-red spectrum for the compound having the structure:

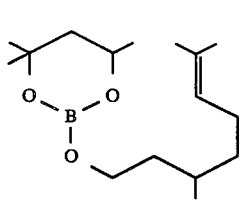

EXAMPLE III

PREPARATION OF 2-(5-PHENYL-3-METHYLPENTYLOXY)-4,4,6-TRIMETHYL-1,3,2-DIOXABORINANE

Reaction:

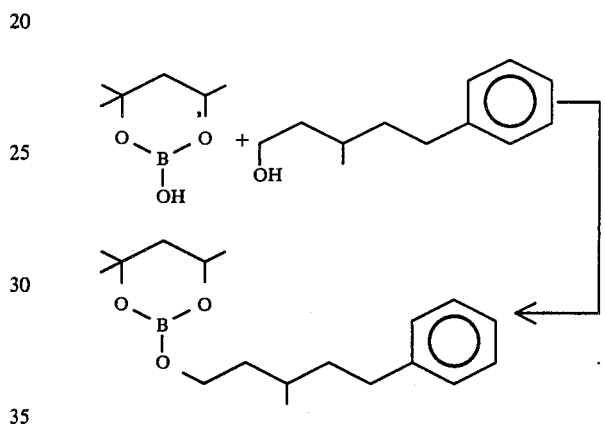

Into a 1 liter reaction vessel equipped with stirrer, thermometer, reflux condenser and heating mantle is placed 409.0 grams of the compound having the structure:

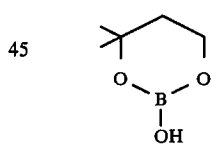

produced according to Example I. Over a period of one hour 354.3 grams of the compound having the structure:

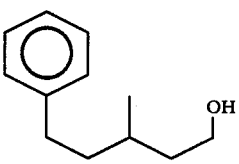

is slowly fed into the reaction mass while maintaining the temperature of the reaction mass at 70° C. At the end of the feeding of the compound having the structure:

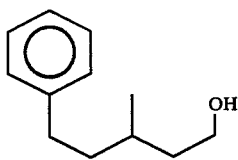

the reaction is heated to 92°–94° C. and maintained at 92°–94° C. for a period of three hours. At the end of the three hour period, the reaction mass is distilled on a 4″ splash column yielding the following fractions:

| Fraction No. | Vapor Temp. (C.) | Liquid Temp. (C.) | Vacuum mm/Hg. Pressure |
|---|---|---|---|
| 1 | 138/167 | 166/172 | 3.0 |
| 2 | 167 | 172 | 3.0 |
| 3 | 167 | 173 | 3.0 |
| 4 | 167 | 174 | 3.0 |
| 5 | 167 | 185 | 3.0 |

Fractions 2, 3 and 4 are bulked.

Bulked fractions 2, 3 and 4 have a rose, muguet and fresh air and ozoney aroma profile with floral, muguet, herbaceous, green and citrusy undertones.

FIG. 6 is the GLC profile for the reaction mixture prior to the reaction. The peak indicated by reference numeral 61 is the peak for the compound having the structure:

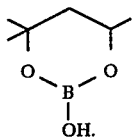

The peak indicated by reference numeral 62 is the peak for the compound having the structure:

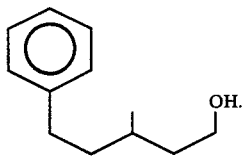

FIG. 7 is the GLC profile for the crude reaction product containing the compound having the structure:

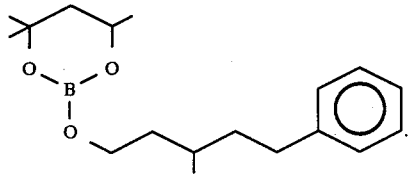

The peak indicated by reference numeral 71 is the peak for the compound having the structure:

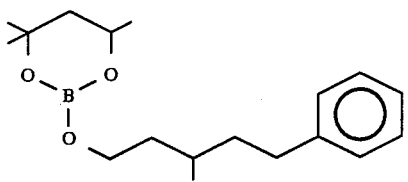

(Conditions: SE-30 column programmed at 100°–220° C. at 8° C. per minute).

FIG. 8 is the NMR spectrum for the compound having the structure:

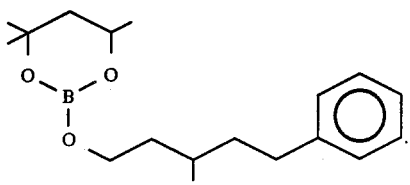

FIG. 9 is the infra-red spectrum for the compound having the structure:

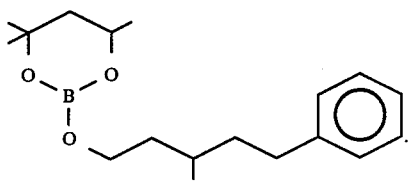

EXAMPLE IV

PREPARATION OF MIXTURE OF 2-(3,4,5,6,6-PENTYLMETHYL-2-HEPTYLOXY)-4,4,6-TRIMETHYL-1,3,2-DIOXABORINANE AND 2-(3,4,5,5,6-PENTYLMETHYL-2-HEPTYLOXY)-4,4,6-TRIMETHYL-1,3,2-DIOXABORINANE

Reaction:

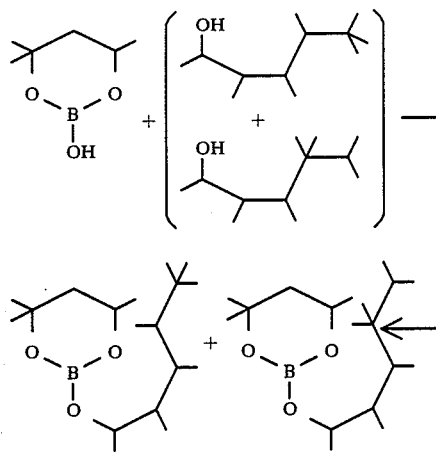

Into a 2 liter reaction vessel equipped with stirrer, thermometer, reflux condenser and heating mantle is placed 409.0 grams of the product of Example I having the structure:

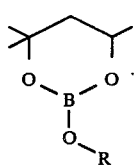

The product is warmed to 70° C. and over a period of one hour 316.2 grams of a mixture of alcohols having the structures:

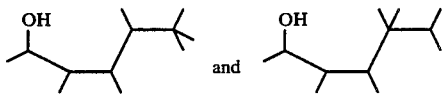

is added to the reaction mass with stirring. The reaction mass is then heated to 85° C. and maintained with stirring at 85° C. for a period of 2.5 hours. At the end of the 2.5 hour period, the reaction mass is distilled on a 12" Goodloe column at 145° C. at 3 mm/Hg. pressure yieldiang a mixture of products having the structures:

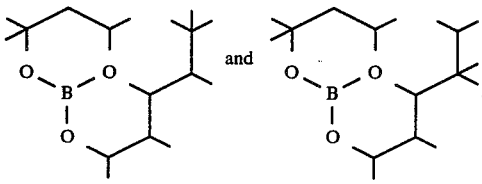

The mixture of compounds having the structures:

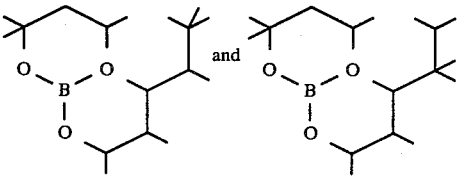

has a woody, piney and camphoraceous aroma profile with woody, peppery and straw-like undertones.

FIG. 10 is the GLC profile for the crude reaction product containing the compounds having the structures:

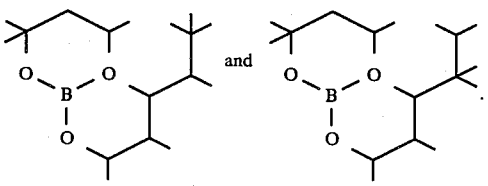

The peak indicated by referance numeral 101 is the peak for the mixture of compounds having the structures:

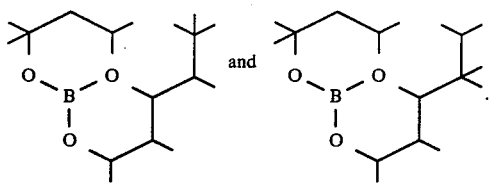

FIG. 11 is the NMR spectrum for the mixture of compounds having the structures:

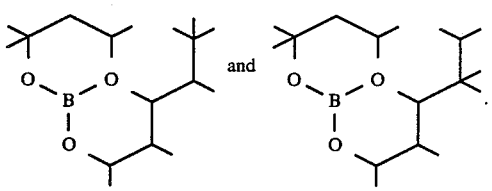

FIG. 12 is the infra-red spectrum for the mixture of compounds having the structures:

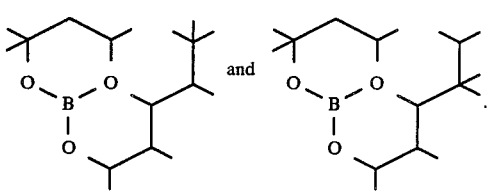

EXAMPLE V

PREPARATION OF 2-(CIS-3-HEXENYLOXY)-4,4,6-TRIMETHYL-1,3,2-DIOXABORINANE

Reaction:

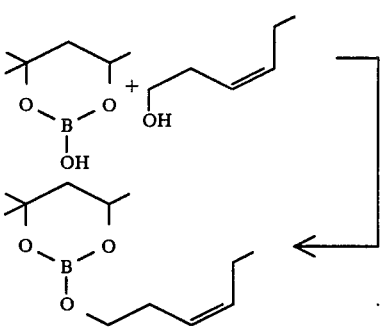

Into a 1 liter reaction vessel equipped with stirrer, thermometer, heating mantle and reflux condenser is placed 133.0 grams of the compound having the structure:

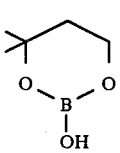

produced according to Example I.

The compound having the structure:

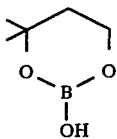

is heated to 70° C. and over a period of one hour 195.0 grams of cis-3-hexenol having the structure:

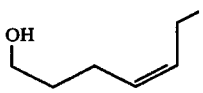

is fed into the reaction vessel. The reaction mass is then heated to 95°–100° C. and maintained at 95°–100° C. over a period of three hours. At the end of the three hour period, the reaction mass is fractionally distilled on a 12" Goodloe column yielding the following fractions:

| Fraction No. | Vapor Temp. (°C.) | Liquid Temp. (°C.) | Vacuum mm/Hg. Pressure |
|---|---|---|---|
| 1 | 90/93 | 95/98 | 3.0 |
| 2 | 94 | 100 | 3.0 |
| 3 | 94 | 100 | 3.0 |

The compound having the structure:

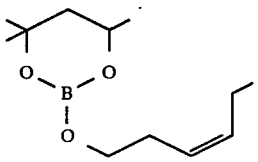

is obtained by bulking fractions 2 and 3.

FIG. 13 is the GLC profile for the reaction mixture prior to the reaction. The peak indicated by reference numeral 131 is the peak for the cis-3-hexenol. The peak indicated by reference numeral 132 is the peak for the compound having the structure:

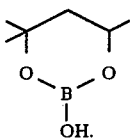

FIG. 14 is the GLC profile for the crude reaction product. The peak indicated by reference numeral 141 is the peak for the cis-3-hexenol reactant. The peak indicated by reference numeral 142 is the peak for the product having the structure:

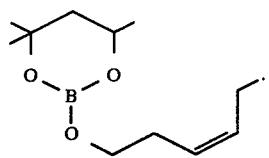

The peak indicated by reference numeral 143 is the peak for the compound having the structure:

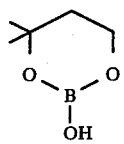

(Conditions: SE-30 column programmed at 100°–220° C. at 8° C. per minute).

FIG. 15 is the NMR spectrum for the compound having the structure:

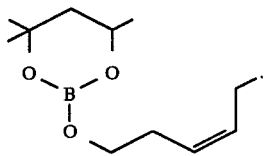

FIG. 16 is is the infra-red spectrum for the compound having the structure:

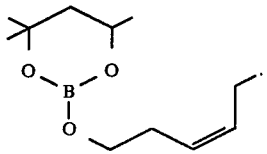

EXAMPLE VI

PERFUMED LIQUID DETERGENTS

Concentrated liquid detergents (lysine salt of n-dodecylbenzene sulfonic acid as more specifically described in U.S. Pat. No. 3,948,818 issued on Apr. 6, 1976 incorporated by reference herein) are prepared containing 0.10%, 0.15%, 0.20%, 0.25%, 0.30% and 0.35% of the compounds having the structure set forth in Table I, supra, and Table II, infra. They are prepared by adding and homogeneously mixing the appropriate quantity of the compounds of Table I, supra, and Table II, infra and the liquid detergent. The detergents all possess excellent aromas set forth in Table II, below, the intensity increasing with greater concentration of compound:

TABLE II

| Compound | Aroma |
|---|---|
| The compound having the structure: | A floral, rose, |

TABLE II-continued

| Compound | Aroma |
|---|---|
| (structure produced according to Example II.) | citrusy aroma profile with muguet and rose undertones. |
| The compound having the structure: (produced according to Example III.) | A rose, muguet and fresh air and ozoney aroma profile with floral, muguet, herbaceous, green and citrusy undertones. |
| Mixture of compounds having the structures: (structures) and (structure) prepared according to Example IV. | A woody, piney and camphoraceous aroma profile with woody, peppery and straw-like undertones. |
| The compound having the structure: (structure) prepared according to Example V. | A leafy, green aroma profile. |
| The compound having the structure: (structure) prepared according to Example XII. | A floral, rose aroma with rose undertones. |

EXAMPLE VII

PREPARATION OF SOAP COMPOSITION

100 Grams of soap chips (per sample) (IVORY® produced by the Procter & Gamble Company of Cincinnati, Ohio), are each mixed with a one gram sample of the compounds set forth in Table II of Example VI, supra until homogeneous compositions are obtained. In each of the cases, the homogeneous compositions are heated under 8 atmospheres pressure, at 180° C. for a period of three hours and the resulting liquids are placed into soap molds. The resulting soap cakes, on cooling, manifest excellent aromas (as set forth in Table II of Example VI, supra) when used in conjunction with water, in a washing sequence.

EXAMPLE VIII

PREPARATION OF SOLID DETERGENT COMPOSITIONS

Detergents are prepared using the following ingredients according to Example I of Canadian Pat. No. 1,007,948 (incorporated by reference herein):

| Ingredient | Percent by Weight |
|---|---|
| NEODOL ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the compounds of Table II of Example, VI, supra. Each of the detergents on contact with water have excellent aromas as set forth in Table II of Example VI, supra.

EXAMPLE IX

Using the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and the perfuming material are as follows:

1. A water "dissolvable" paper ("Dissolvo Paper");
2. Adogen 448 (m.p. about 140° F.) as the substrate coating; and
3. An outer coating having the following formulation (m.p. about 150° F.):
   57%: $C_{20\text{-}22}$ HAPS
   22%: isopropyl alcohol
   20%: antistatic agent
   1%: of one of the compounds as set forth in Table II of Example VI, supra.

Fabric softening compositions prepared according to Example I at column 15 of U.S. Pat. No. 3,632,396 having aromas as set forth in Table II of Example VI, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. Each of the compounds of Table II of Example VI, supra, is admixed in each case with the outer coating mixture, thereby providing a total aromatized outer coating weight ratio of substrate of about 0.5:1 by weight of the substrate. Pleasant aromas are provided (as indicated in Table II of Example VI, supra) to the head space in a dryer on operation thereof in each case using said drier-added fabric softener non-woven fabrics.

EXAMPLE X

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 Grams of the polymer is dissolved in the alcohol. The following ingredients are added to the PVP/VA alcoholic solution:

| Ingredient | Weight Percent |
| --- | --- |
| Dioctyl sebacate | 0.05 |
| Benzyl alcohol | 0.10 |
| Dow Corning 473 fluid prepared by the Dow Corning Corporation | 0.10 |
| Tween 20 surfactant (prepared by ICI America Corporation) | 0.03 |
| One of the compounds of Table II of Example VI, supra. | 0.10 |

Each of the compounds of Table II of Example VI, supra, on use of the pump hair spray provides an aesthetically pleasing aroma as indicated in Table II of Example VI, supra to the hair when the pump hair spray is used on moist hair.

EXAMPLE XI

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stephanol WAT produced by the Stephan Chemical Compamy (35.0 weight percent). The resulting mixture is heated to 60° C. and mixed until a clear solution is obtained (at 60° C.). This material is "Composition A".

GAFOUAT® 755N polymer (manufactured by GAF Corporation of 140 West 51st Street, New York, N.Y.) (5.0 weight percent) is admixed with 0.1 weigt percent sodium sulfite and 1.4 weight percent polyethylene glycol 6000 distearate produced by Armak Corporation. This material is "Composition B".

Separately the resulting "Composition A" and "Composition B" are then mixed in a 50:50 weight ratio of A:B and cooled to 45° C. and 0.3 weight percent of each of the compounds set forth in Table II of Example VI, supra is added to the mixture. The resulting mixtures are cooled to 40° C. and blending is carried out for an additional one hour in each case. At the end of these blending periods the resulting materials on contact with water provide pleasant fragrances as set forth in Table II of Example VI, supra.

EXAMPLE XII

PREPARATION OF GERANYLOXY-1,3,2-DIOXABORINANE

Reaction:

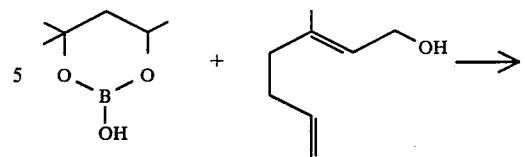

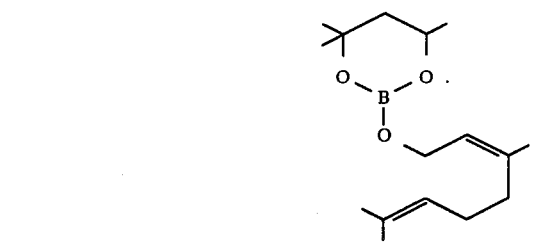

Into a 2 liter flask equipped with apparatus for providing a nitrogen blanket and Bidwell trap are placed the following materials:
347.0 grams of Geraniol (2.25 moles);
250.0 ml cyclohexane;
299.0 grams of the compound having the structure:

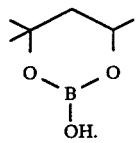

The reaction mass is then heated up and water of reaction is azeotroped out. The reaction mass is maintained at a temperature of 104–107 C. for a period of 12 hours. During this period a total of 21 cc's of water is removed. The reaction mass is then distilled on a 4" splash column yielding the following fractions:

| Fraction No. | Vapor Temp. (°C.) | Liquid Temp. (°C.) | Vacuum mm/Hg. Pressure | Weight of Fraction |
| --- | --- | --- | --- | --- |
| 1 | 114/143 | 149/148 | 3.2 | 31.0 |
| 2 | 143 | 147 | 2.8 | 27.0 |
| 3 | 143 | 147 | 2.8 | 30.0 |
| 4 | 143 | 147 | 2.8 | 30.0 |
| 5 | 145 | 148 | 2.8 | 32.0 |
| 6 | 145 | 149 | 2/8 | 30.0 |
| 7 | 145 | 150 | 2.8 | 30.0 |
| 8 | 146 | 150 | 2.8 | 25.0 |
| 9 | 146 | 150 | 2.8 | 31.0 |
| 10 | 146 | 150 | 2.8 | 30.0 |
| 11 | 146 | 150 | 2.8 | 27.0 |
| 12 | 146 | 150 | 2.8 | 28.0 |
| 13 | 146 | 150 | 2.8 | 27.0 |
| 14 | 145 | 150 | 2.8 | 25.0 |
| 15 | 146 | 150 | 2.8 | 29.0 |
| 16 | 146 | 151 | 2.8 | 30.0 |
| 17 | 146 | 153 | 2.8 | 28.0 |
| 18 | 146 | 155 | 2.8 | 28.0 |
| 19 | 146 | 157 | 2.8 | 13.0 |

FIG. 19 is the GLC profile for the crude reaction product containing the compound having the structure:

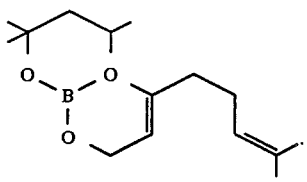

FIG. 20 is the GLC profile for fraction 13 of the foregoing distillation (Conditions: SE-30 column programmed at 100°–220° C. at 16° C. per minute).

FIG. 21 is the NMR spectrum for the compound having the structure:

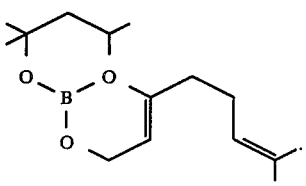

FIG. 22 is the infra-red spectrum for the compound having the structure:

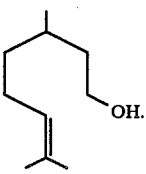

Bulked distillation fractions 7–13 has a floral, rose aroma with rose undertones.

What is claimed is:

1. A 1,3,2-Dioxaborinane derivative defined according to the genus:

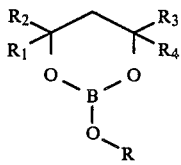

wherein $R_1$, $R_2$, $R_3$ and $R_4$ are the same or different hydrogen, methyl and ethyl; and wherein R represents $C_6$ straight chain alkenyloxy; $C_{10}$ branched chain alkenyloxy; $C_{12}$ aralkoxy; $C_{12}$ branched chain alkoxy; or $C_{10}$ branched chain alkadienyloxy.

2. The 1,3,2-Dioxaborinane derivative of claim 1 having the structure:

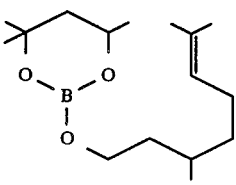

3. The 1,3,2-dioxaborinane derivative of claim 1 having the structure:

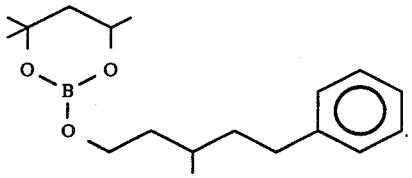

4. The 1,3,2-dioxaborinane derivative of claim 1 having the structure:

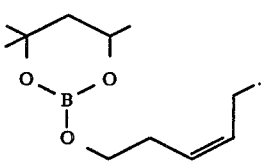

5. The 1,3,2-dioxaborinane derivative of claim 1 having the structure:

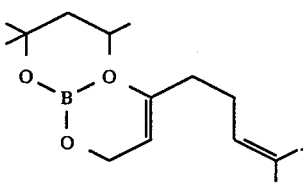

6. The composition of claim 1 being a mixture of compounds having the structures:

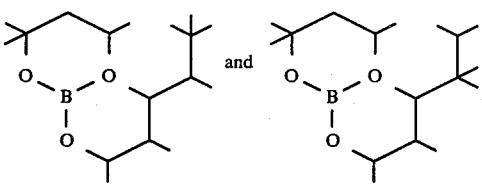

7. A perfumed article containing a base and intimately admixed with said base at least one 1,3,2-dioxaborinane derivative defined according to claim 1.

8. A process for augmenting or enhancing the aroma of a perfume composition, cologne, perfumed polymer or perfumed article on contact with water or water vapor comprising the step of intimately admixing said perfume composition, cologne, perfumed article or perfumed polymer with at least one 1,3,2-dioxaborinane derivative defined according to claim 1 and then contacting said perfume composition, perfumed article, perfumed polymer or cologne with water or water vapor.

9. The process of claim 8 wherein the borinane compound has the structure:

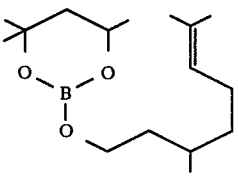

10. The process of claim 8 wherein the borinane compound has the structure:

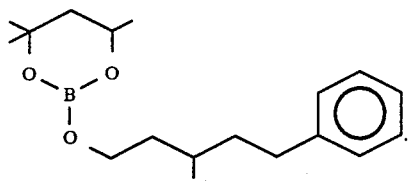

11. The process of claim 8 wherein the borinane compound has the structure:

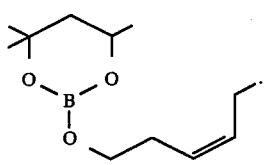

12. The process of claim 8 wherein the borinane compound has the structure:

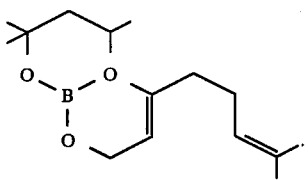

13. The process of claim 8 wherein the bornane compounds have the structures:

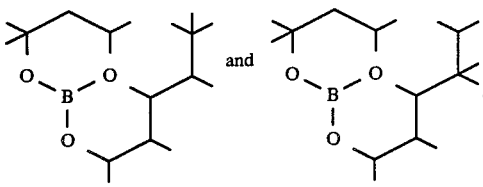

14. The process of claim 7 wherein the borinane compound is admixed with the perfumed article and the perfumed article is a solid or liquid anionic, cationic, nonionic or zwitterionic detergent.

15. The process of claim 7 wherein the borinane compound is admixed with a perfumed article and the perfumed article is a fabric softener composition or drier-added fabric softener article.

16. The process of claim 7 wherein the borinane compound is admixed with a perfumed article and the perfumed article is a hair preparation.

17. A perfumed polymer consisting essentially of a microporous polymer containing interconnected voids and filling said interconnected voids a perfumery composition containing a substantial quantity of at least one 1,3,2-dioxaborinane derivative defined according to claim 1.

* * * * *